United States Patent
Criddle et al.

(10) Patent No.: US 9,062,340 B2
(45) Date of Patent: Jun. 23, 2015

(54) PROCESS FOR THE SELECTION OF PHB-PRODUCING METHANOTROPHIC CULTURES

(75) Inventors: Craig S. Criddle, Redwood City, CA (US); Katherine H. Rostkowski, Washington, DC (US); Eric R. Sundstrom, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 263 days.

(21) Appl. No.: 13/590,603

(22) Filed: Aug. 21, 2012

(65) Prior Publication Data

US 2013/0052681 A1  Feb. 28, 2013

Related U.S. Application Data

(60) Provisional application No. 61/526,824, filed on Aug. 24, 2011, provisional application No. 61/653,281, filed on May 30, 2012.

(51) Int. Cl.
  *C12Q 1/04* (2006.01)
  *C12P 1/00* (2006.01)
  *C12P 1/04* (2006.01)

(52) U.S. Cl.
  CPC ..................................... *C12Q 1/04* (2013.01)

(58) Field of Classification Search
  None
  See application file for complete search history.

(56) References Cited

PUBLICATIONS

Pfluger et al. Bioresource Technology, vol. 102, 2011, p. 9919 to 9926.*
Nyerges et al. Applied and Environmental Microbiology vol. 76, No. 16, 2010, p. 5648-5651.*
Kalyuzhnaya et al Appl. Environ. Microbiol. 2006, vol. 72, No. 6 p. 4293-4301.*

* cited by examiner

*Primary Examiner* — Chris R Tate
*Assistant Examiner* — Douglas F White
(74) *Attorney, Agent, or Firm* — Lumen Patent Firm

(57) ABSTRACT

A method of selection for type II methanotrophs is provided that includes enriching a microbial feedstock using a non-sterile bioreactor with a methane source and a nitrogen source, where the microbial feedstock includes a mixture of Type I and Type II methanotrophic cells, where an inhibited growth of the Type I methanotrophic cells and an enhanced growth of the Type II methanotrophic cells forms. The method further includes exposing intermittently the enriched microbial feedstock to i) nitrate, ii) urea, or i) and ii), where enhanced growth of the Type II methanotrophs is established, and exposing the Type II methanotrophs to an unbalanced growth condition where production of polyhydroxybutyrate is induced.

7 Claims, 15 Drawing Sheets

(c)

(d)

*(e)*

(a)

(b)

(c)

(d)

(e)

(f)

PROCESS FOR THE SELECTION OF PHB-PRODUCING METHANOTROPHIC CULTURES

CROSS-REFERENCE TO RELATED APPLICATIONS

This application claims priority from U.S. Provisional Patent Application 61/526,824 filed Aug. 24, 2011, which is incorporated herein by reference. This application claims priority from U.S. Provisional Patent Application 61/653,281 filed May 30, 2012, which is incorporated herein by reference.

FIELD OF THE INVENTION

The invention relates generally to methods and systems for producing bioplastics such as polyhdroxyalkanoates (PHAs) that include Poly(3-hydroxy)butyrates (PHBs). More specifically, the invention relates to such methods and systems that produce PHB in mixed culture conditions from substrates including biogas and natural gas.

BACKGROUND OF THE INVENTION

As environmental concerns increase over the production and disposal of conventional petrochemical-based plastics, there is a growing incentive to find a method of producing inexpensive alternatives. Bioplastics have numerous advantages over petrochemical-based plastics. Unlike petrochemical-based plastics, bioplastics rapidly biodegrade and are non-toxic. Bioplastics are derived from renewable resources, decreasing demand for non-renewable petrochemical resources. Bioplastics have lower energy inputs than petrochemical-based plastics, and their production results in lower $CO_2$ emissions than petrochemical plastic production. It is therefore of great interest to find improved methods for producing bioplastics.

Bioplastics include various biopolymers such as polyhydroxyalkanoates (PHA), and particularly the polymer of hydroxybutyrate, polyhydroxybutyrate (PHB). PHAs are polyesters with repeating subunits (100-30,000) that have the formula $-[O-CH(R)(CH2)xCO]-$.

The most common type of PHA is PHB, where $R=CH_3$ and x=1. Another is polyhydroxy valerate (PHV), where $R=CH_2CH_3$ and x=1. PHAs are produced by many bacteria under unbalanced growth conditions when they have access to surplus carbon but lack an essential nutrient, such as phosphorus, nitrogen, sulfur, iron, sodium, potassium, magnesium, or manganese. Under these conditions, the bacteria hoard the carbon, storing it as intracellular PHA granules. The granules are consumed when supplies of carbon and energy become limiting or when the limiting nutrient again becomes available.

The most common known methods of PHA production use pure cultures, relatively expensive fermentable substrates, as sugar from corn, and aseptic operation. The price of PHA produced using this feedstock and methodology currently exceeds the price needed to be competitive with petrochemical-based plastics. Thus, an important challenge is to provide improved methods for producing PHAs that are more efficient and less expensive, so that bioplastics can become commercially competitive with petrochemical-based plastics. Some methanotrophs have been shown to produce PHBs from methane under nutrient limited conditions. The PHB-producing potential of most methanotrophic species, however, remains largely unexplored, as are methods for efficient and inexpensive biosynthesis of PHB.

PHB production is widespread but not universal amongst wild-type methanotrophs. Type II methanotrophs are known to naturally produce PHB while PHB production has not been documented in type I methanotrophs. In mixed culture growth, PHB production is therefore contingent upon selective growth conditions that allow for rapid growth of type II methanotrophs while inhibiting the growth of type I methanotrophs. Currently known selection methods unrelated to nitrogen source manipulation include growth at low pH, growth with no copper in the growth medium, and growth in dilute medium. Continuous growth on ammonium, urea, dinotrogen gas or hydroxylamine has been shown previously. Continuous growth on these nitrogen sources severely limits either growth rates or selectively, while intermittent addition according to the current invention has no such constraints and is therefore a suitable technology for large scale production.

What is needed is a method of selecting Type II methanotrophs from a mixture of Type I and Type II methanotrophic cells, where inhibited growth of the Type I methanotrophic cells and an enhanced growth of the Type II methanotrophic cells forms

SUMMARY OF THE INVENTION

To address the needs in the art, a method of selection for type II methanotrophs is provided that includes enriching a microbial feedstock using a non-sterile bioreactor with a methane source and a nitrogen source, where the microbial feedstock includes a mixture of Type I and Type II methanotrophic cells, where an inhibited growth of the Type I methanotrophic cells and an enhanced growth of the Type II methanotrophic cells forms. The method further includes exposing intermittently the enriched microbial feedstock to i) nitrate, ii) urea, or i) and ii), where enhanced growth of the Type II methanotrophs is established, and exposing the Type II methanotrophs to an unbalanced growth condition where production of polyhydroxybutyrate is induced.

According to one aspect of the invention, the nitrogen source can include ammonium, hydroxylamine, nitrite, or dinotrogen gas.

In another aspect of the invention, the unbalanced growth condition includes limiting nutrients during a growth phase of the Type II methanotrophic cells. In one aspect the limited nutrients can include nitrogen, phosphorus, calcium, copper, potassium, iron, magnesium, or sulfur.

In a further aspect of the invention, ammonium, hydroxylamine, or ammonium and hydroxylamine are used to inhibit growth of the type I methanotrophs in conjunction with additional nitrogen sources. In one aspect the additional nitrogen sources include a nitrate source or a urea source.

In yet another aspect of the invention, methane, biogas, methane and oxygen, or biogas and oxygen is provided continuously to the Type II methanotrophic cells.

According to one aspect of the invention, PHB consumption is concurrent with exposure to the nitrogen sources.

In another aspect of the invention, methane or oxygen is reduced or eliminated in the bioreactor during exposure to the nitrogen sources.

In a further aspect of the invention, the bioreactor is operated as a sequencing batch bioreactor.

According to another aspect of the invention, concentrations of the nitrogen sources are varied to promote growth of methanotrophs or inhibit growth of type I methanotrophs.

According to another embodiment of the invention, a method of selection for type II methanotrophs is provided that includes enriching a microbial feedstock, using a non-sterile bioreactor, with methane and a nitrogen source, where the microbial feedstock includes a mixture of Type I and Type II methanotrophic cells, where an inhibited growth of the Type I methanotrophic cells and an enhanced growth of the Type II methanotrophic cells forms, where the nitrogen source is varied periodically and/or the methane source is varied periodically. Regarding the periodic nitrogen variation, periodic nitrogen concentration reductions and concentration returns causes a partial pressure of the methane concentration to increase according to the reduction, where the methane partial pressure increase results in a decrease of the ammonium inhibition of the enhanced growth of said Type II methanotrophic cells. Alternatively, the periodic methane variation includes a methane concentration increase such that there is a reduction of the ammonium inhibition of the enhanced growth of the Type II methanotrophic cells.

DETAILED DESCRIPTION

Figure 1:
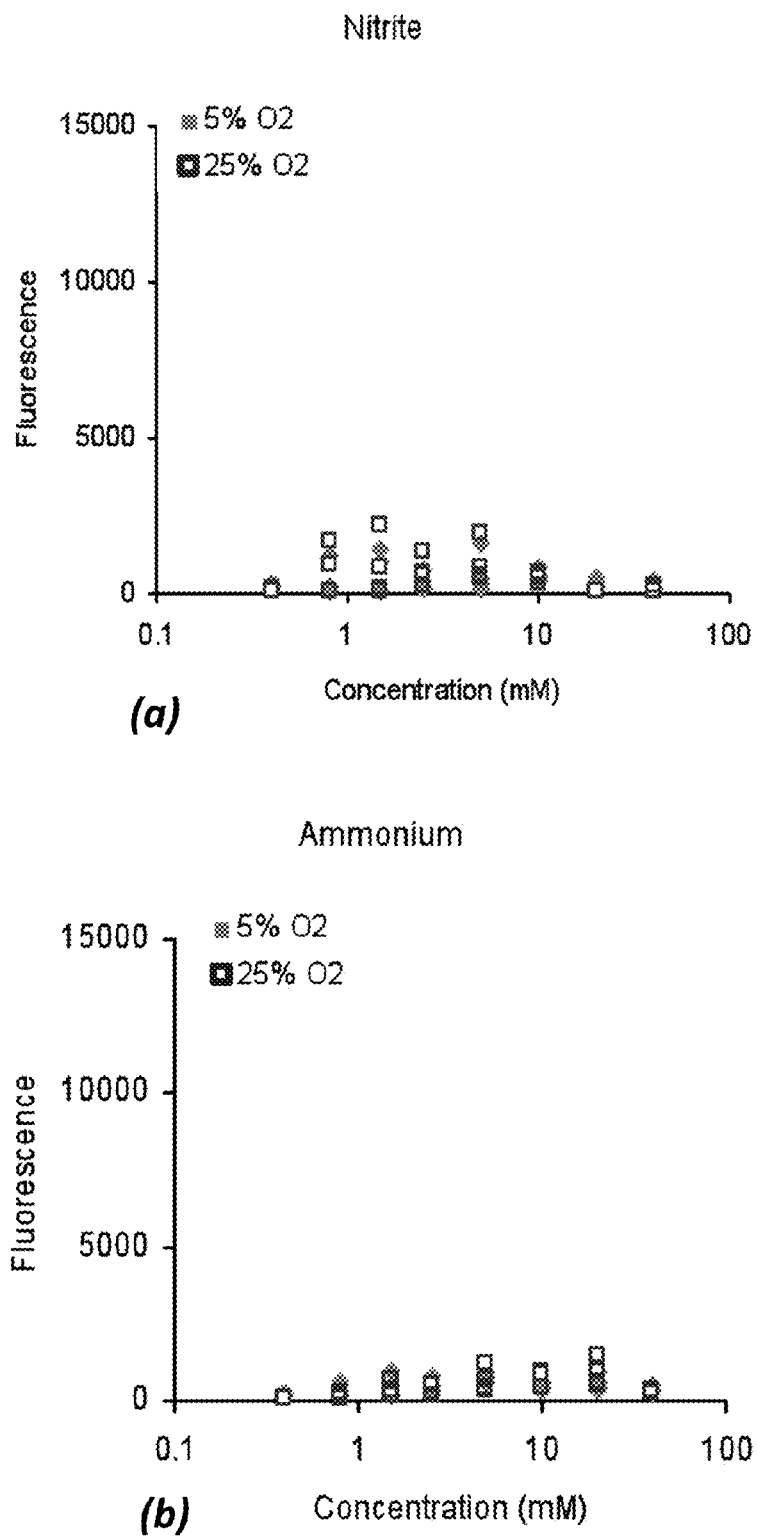
FIGS. 1a-1e show competition among mixed cultures, according to one embodiment of the invention.
Figure 1:
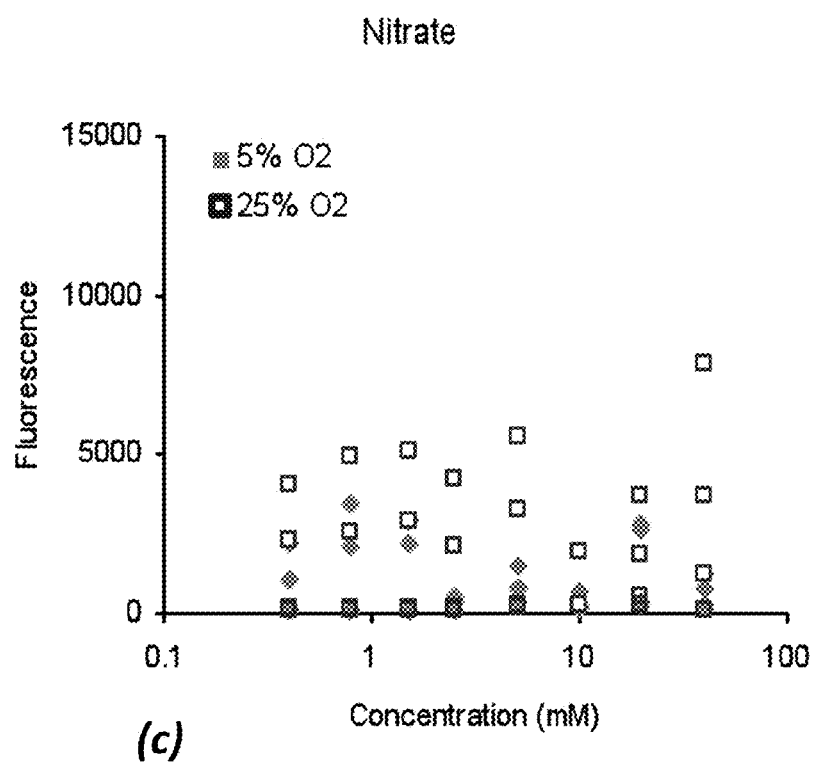
Figure 1:
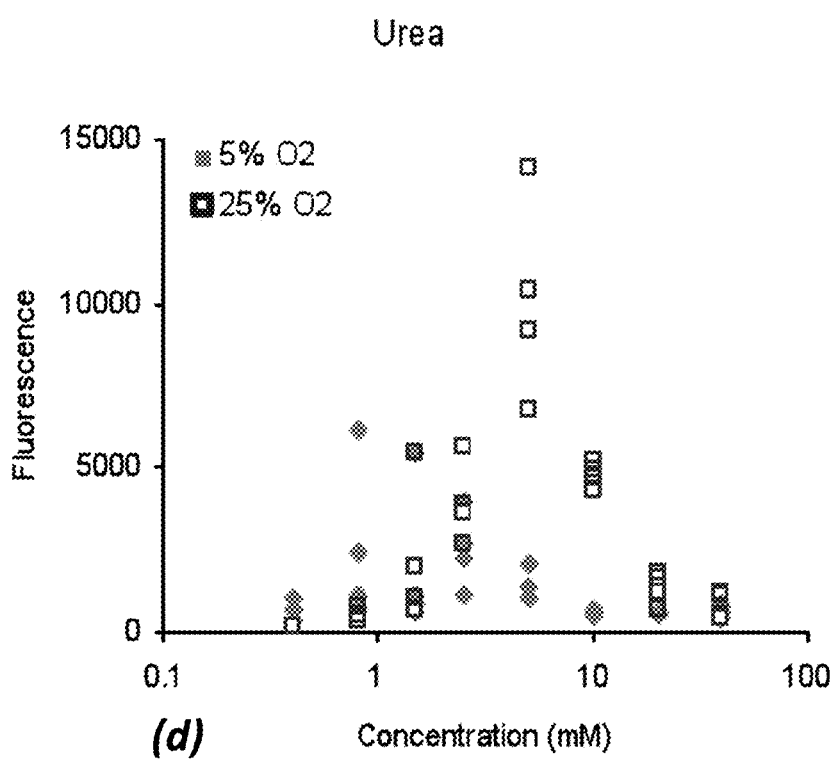
Figure 1:
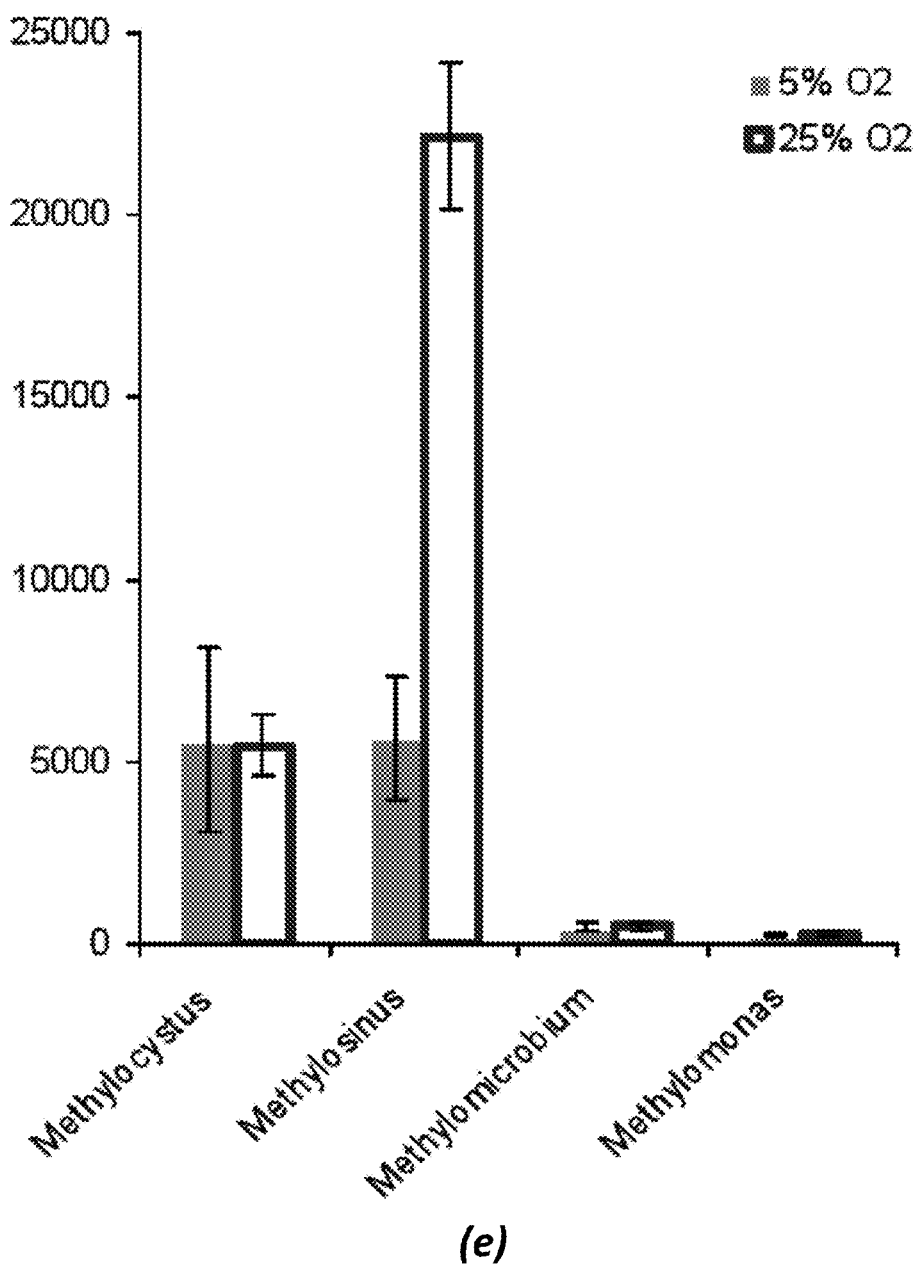
Figure 2:
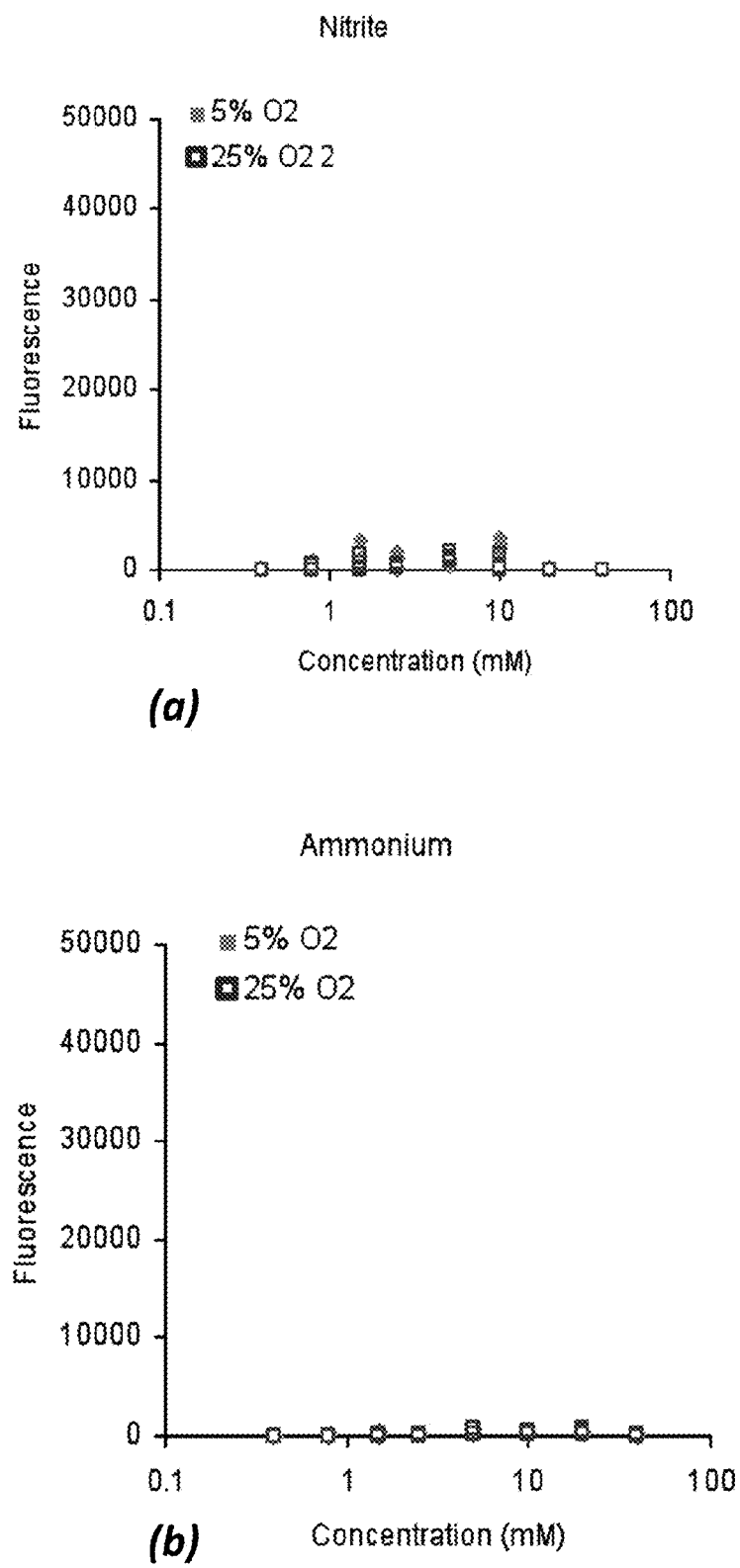
FIGS. 2a-2e further show competition among mixed cultures, according to one embodiment of the invention.
Figure 2:
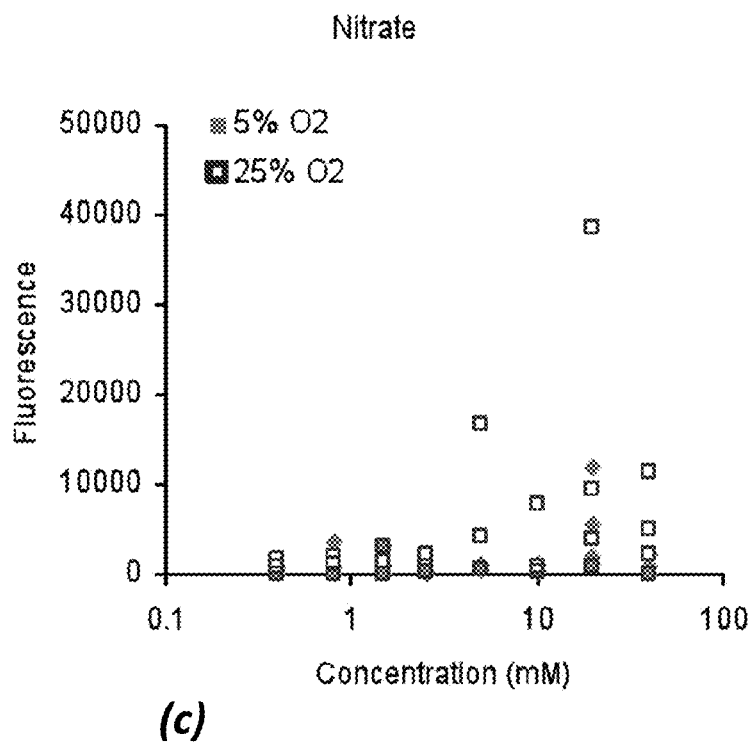
Figure 2:
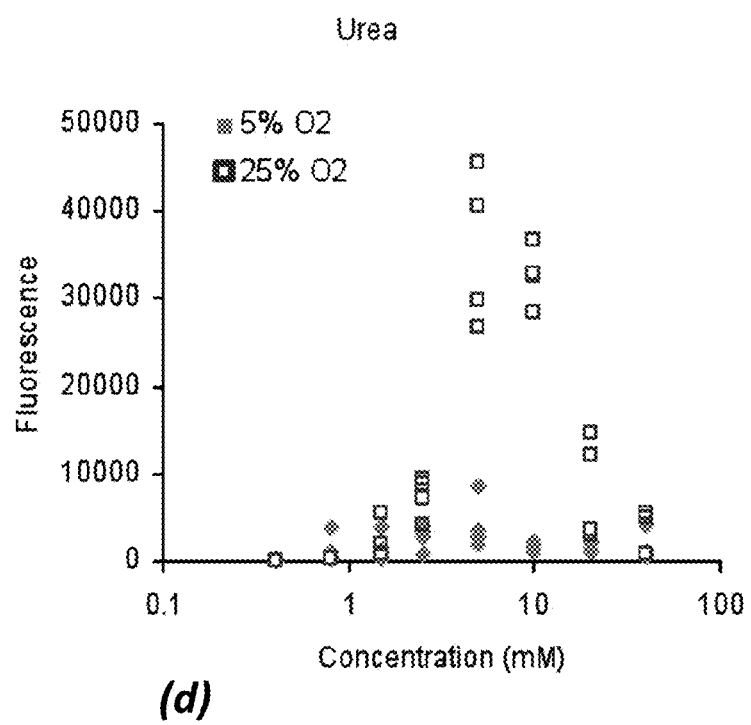
Figure 2:
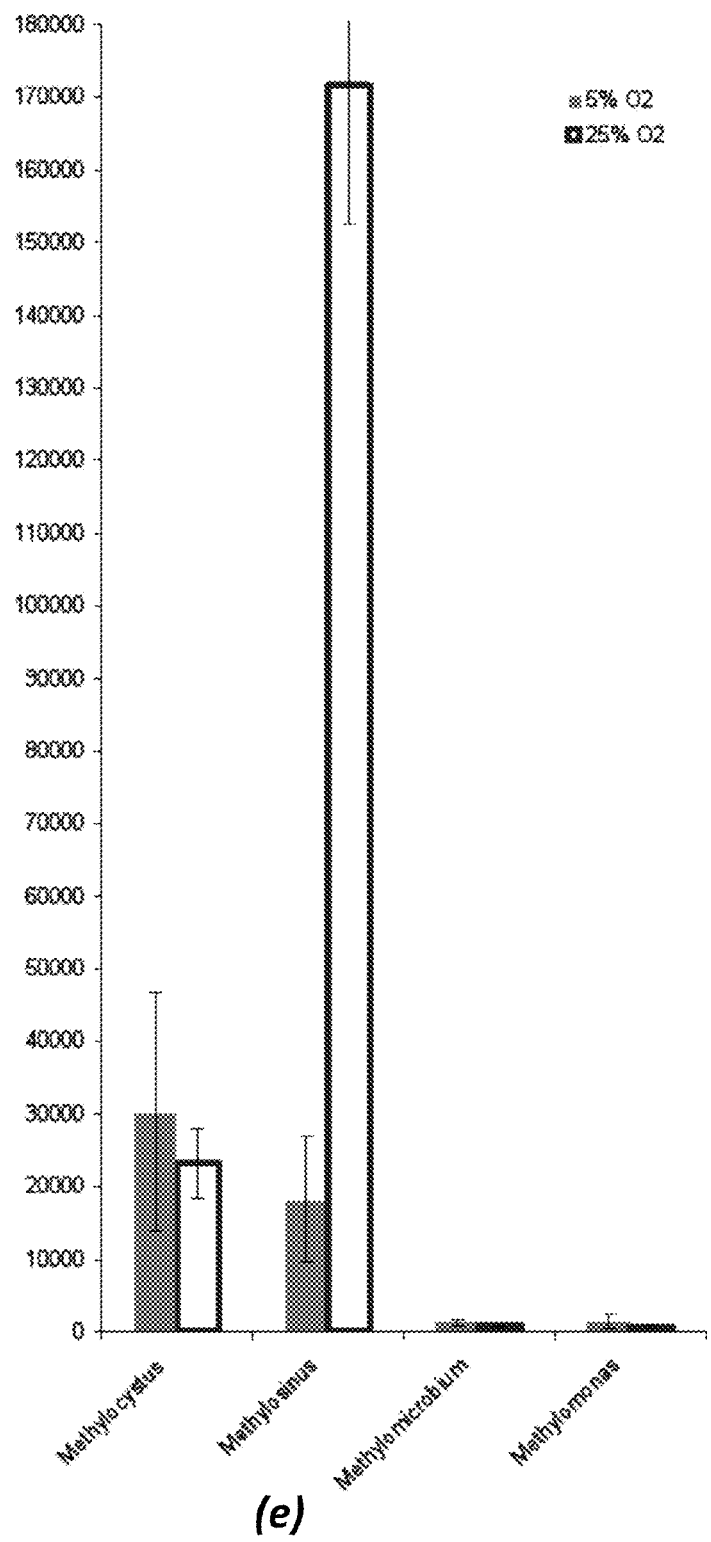
Figure 3:
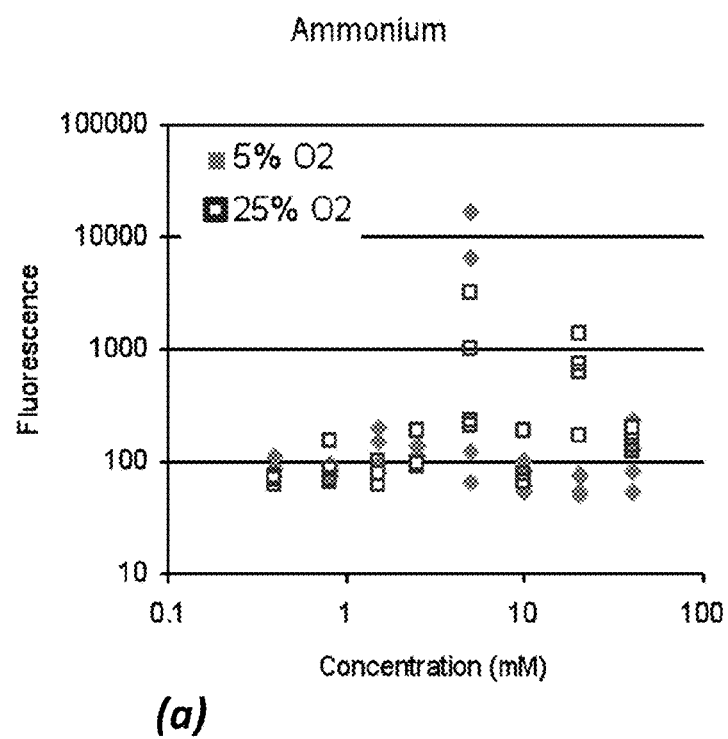
FIGS. 3a-3f show enrichments from activated sludge containing a diverse and unquantified consortium of methanotrophs and other organisms.
Figure 3:
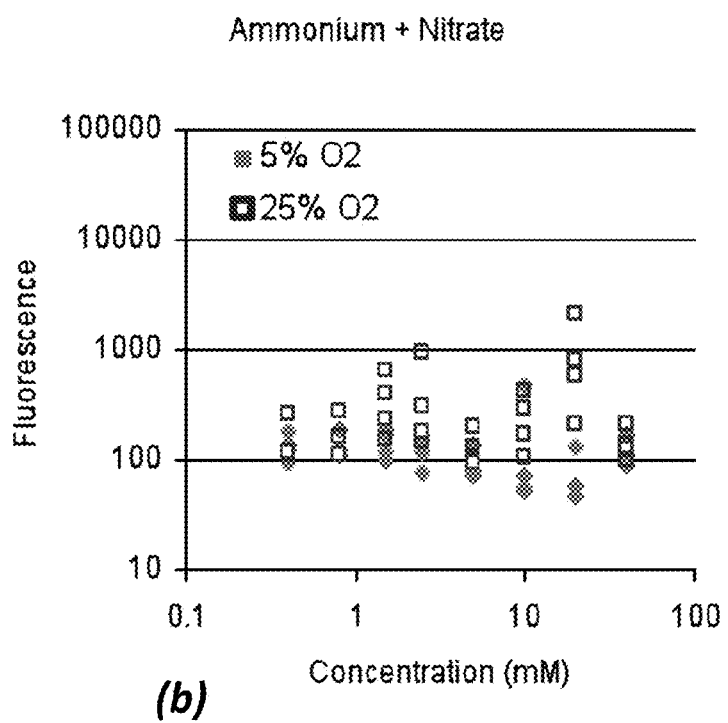
Figure 3:
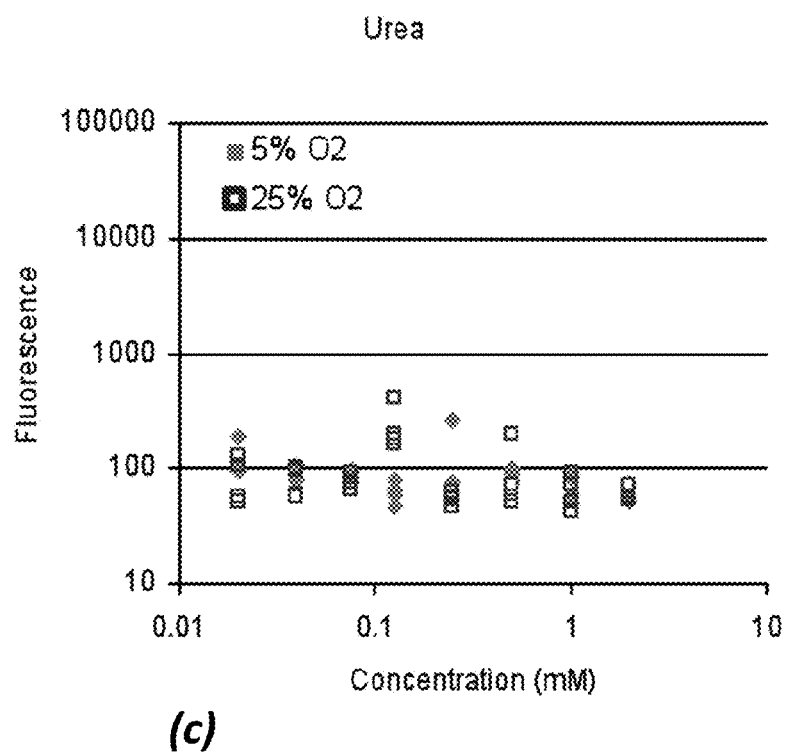
Figure 3:
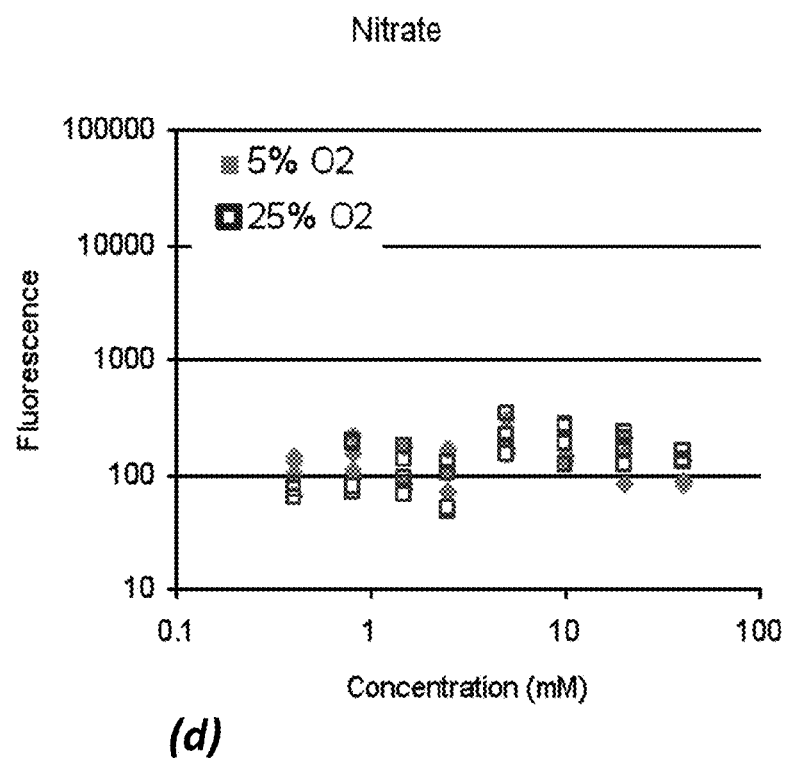
Figure 3:
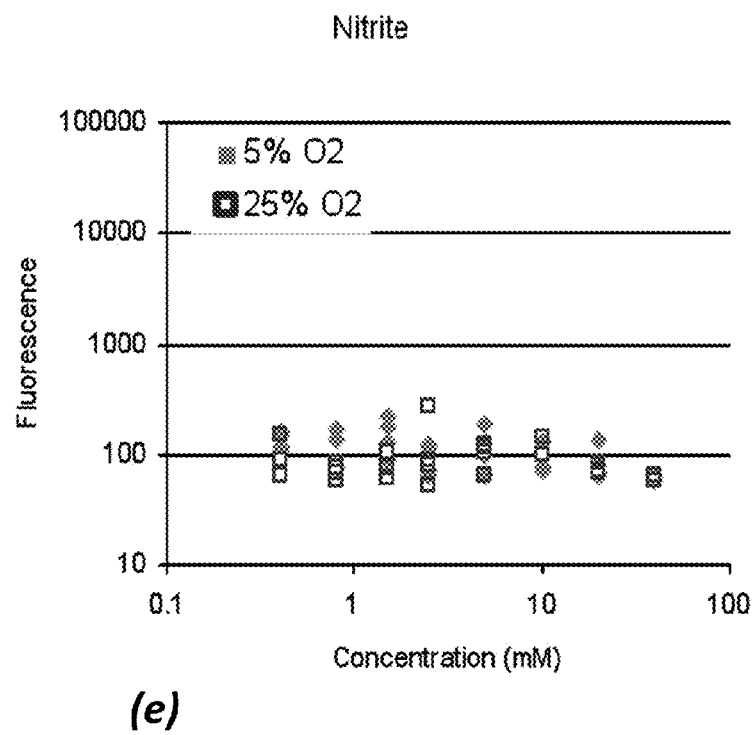
Figure 3:
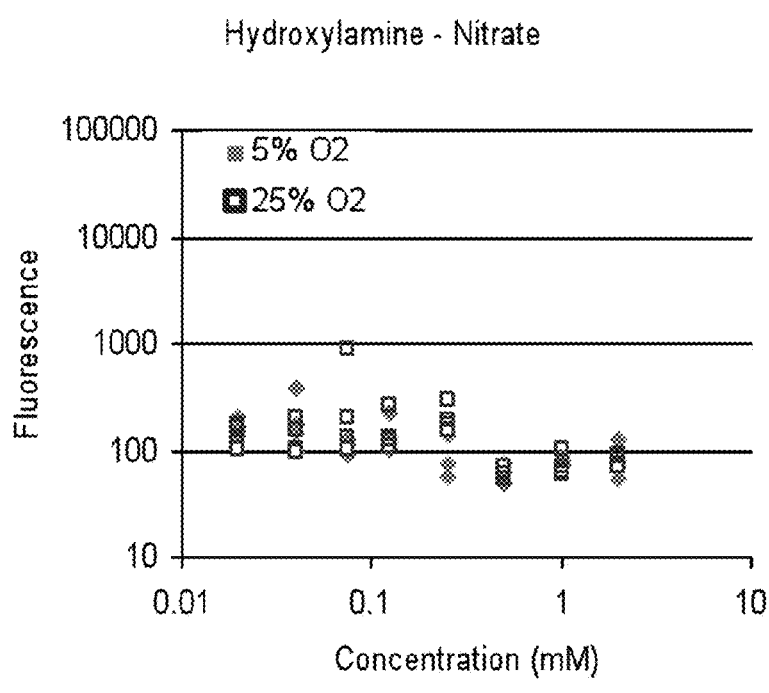
Figure 4:
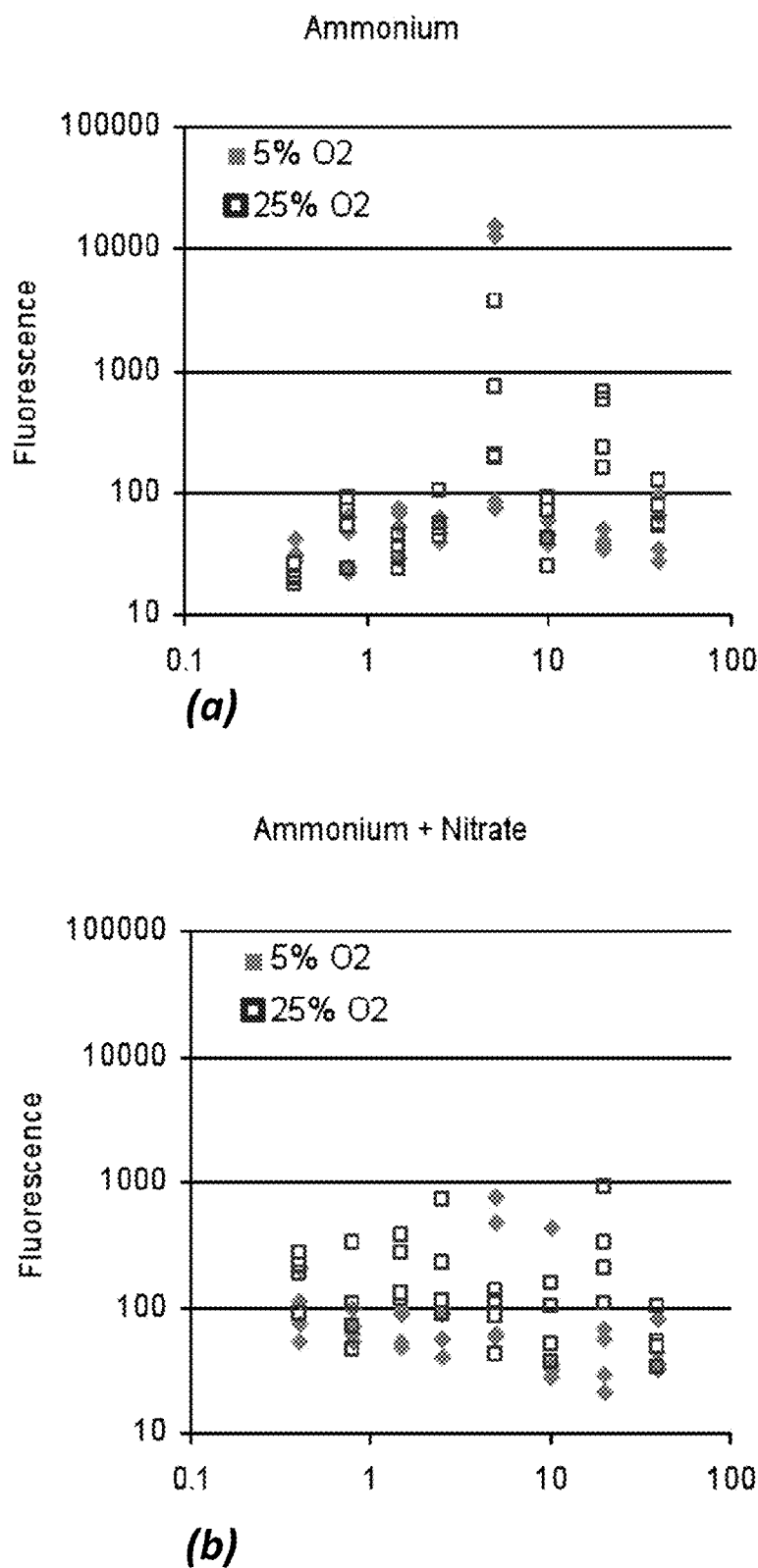
FIGS. 4a-4f further show enrichments from activated sludge containing a diverse and unquantified consortium of methanotrophs and other organisms.
Figure 4:
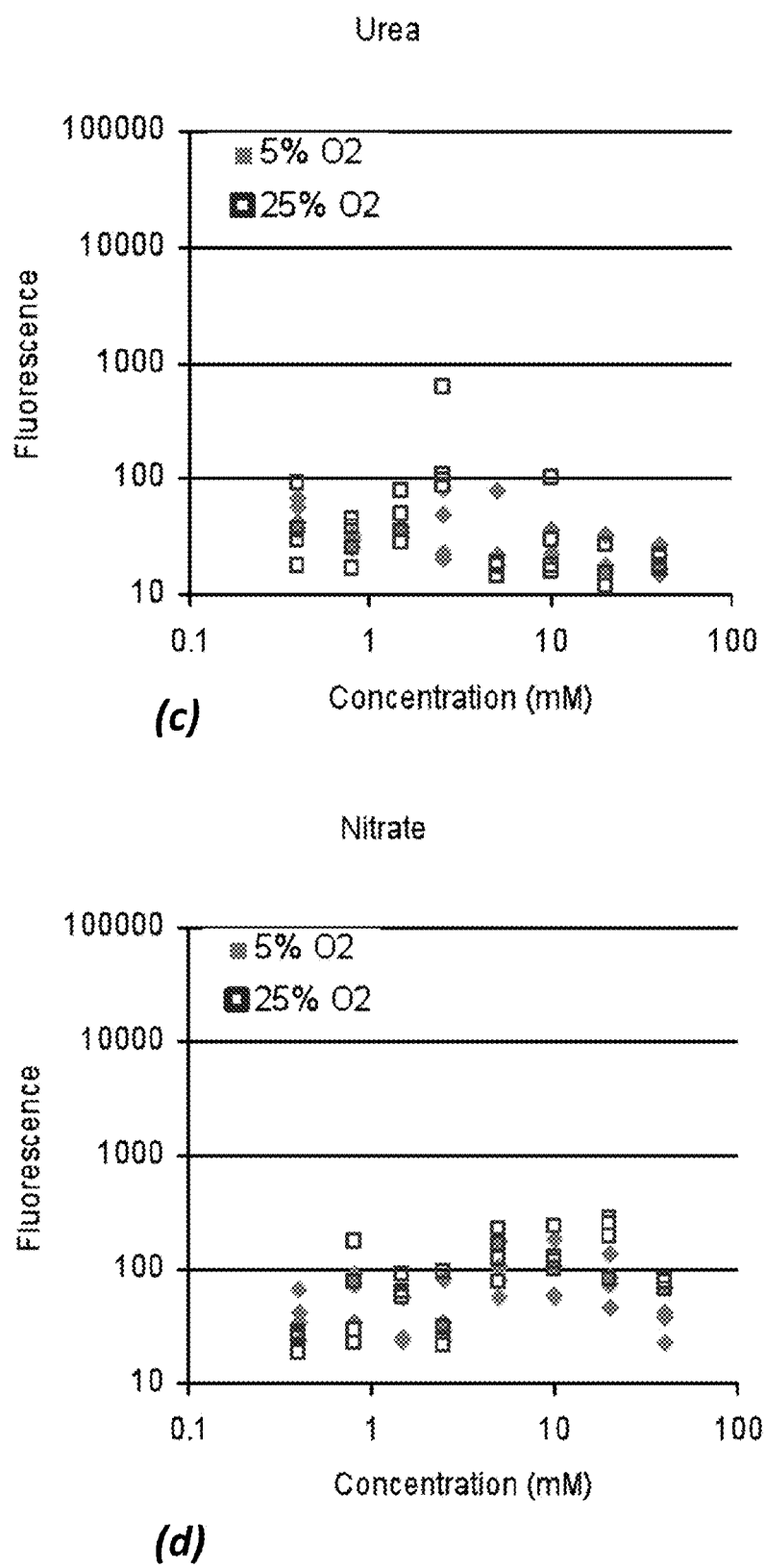
Figure 4:
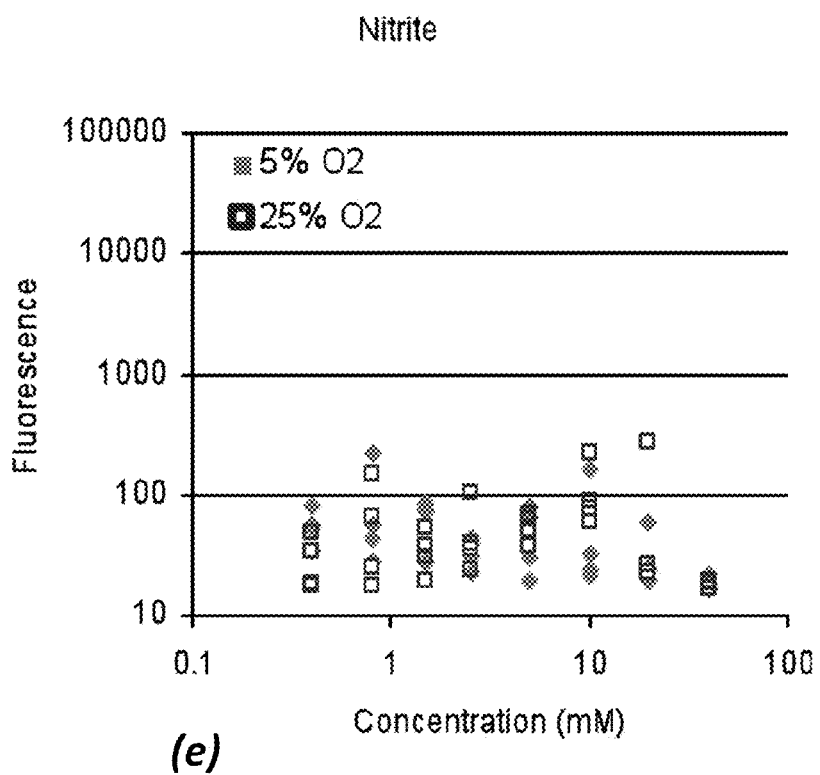
Figure 4:
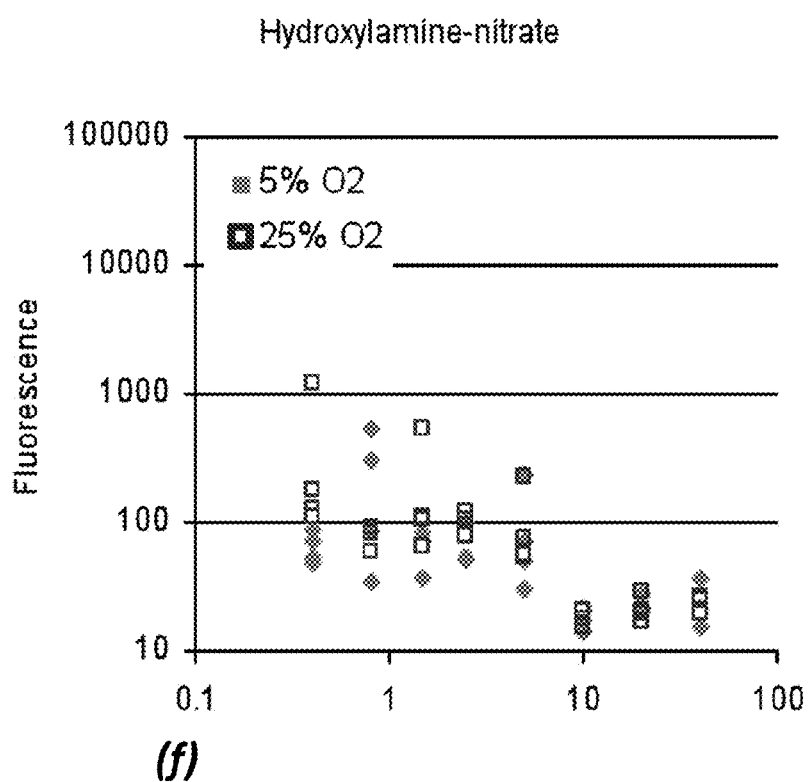

To address the problems associated with wide-spread synthetic polymer (plastic) use that includes the use of nonrenewable resources, persistence, and ecological and health impacts, without compromising the product's convenience, embodiments of the present invention provide methods and systems to replace it with a biodegradable and biocompatible equivalent. Polyhydroxyalkanoates (PHAs), such as polyhydroxybutyrate (PHB), are intracellular carbon and energy storage compounds synthesized by many bacteria. PHAs have properties similar to conventional plastics. Cost effective PHB production is possible through use of waste carbon as a substrate combined with low cost nutrient delivery strategies. Production of PHBs by type II methanotrophs uses a low-cost, abundant greenhouse gas. Since type II methanotrophs fix nitrogen, the present invention uses nitrogen-fixation for selection of PHB-producing methanotrophs.

Microorganisms within the alpha-proteobacteria group possess both the ability to produce polyhydroxyalkanoate storage polymers and fix nitrogen. One aspect of the current invention enables enrichment and maintenance of PHA-accumulating cultures from a diverse inoculum to provide new and useful results. It enables facile selection and maintenance of microbial communities that can accumulate PHA.

The invention makes use of the principle of eco-biotechnology, a strategy based on natural selection and competition rather than on genetic or metabolic engineering, also known as selective pressure for product formation. According to a further aspect, the invention avoids sterilization requirements, enables adaptation, permits use of mixed substrates, and is well suited for continuous processes. Conversely, other known processes use pure cultures that require well-defined feedstocks and aseptic process conditions, have high substrate costs, expensive equipment, high energy consumption, and are thus may be less attractive for scale-up and production.

According to one aspect of the invention, PHA-producing microorganisms are selectively enriched from a microbially diverse inoculum (e.g. activated sludge at a wastewater treatment plant or soil) using dinitrogen gas ($N_2$) as the primary source of nitrogen for growth. This process can be used to select for or maintain a high PHA-producing culture over long time periods. In one embodiment, a growth medium containing a carbon substrate(s) inoculated with a microbially diverse inoculum (e.g. activated sludge at a wastewater treatment plant or soil) and dinitrogen gas ($N_2$) is supplied as the primary nitrogen source. This selects for alpha proteobacteria capable of PHA accumulation. In a subsequent step, the carbon substrate(s) are provided under unbalanced growth conditions, when another essential nutrient is limiting to growth and PHA accumulation occurs.

In some example experiments, activated sludge was used as the inoculum for enrichment of cultures that used methane as the sole carbon source and nitrogen gas as the sole nitrogen source. PHB production was induced by limiting nitrogen and quantified by gas chromatography. Results were compared to controls that received nitrate as the nitrogen source. Terminal restriction fragments revealed shifts in community structure. Under nitrogen-fixing conditions, PHB production was 44.3±1.4% by mass, while PHB production in nitrate-fed cultures was 2.3±0.3%, showing a strong selective pressure. Methane addition and nitrogen-fixation shifted the community structure to one dominated by PHB-producing type II methanotrophs. Thus, nitrogen gas can be effectively used for selection of PHB-producing type II methanotrophs, as evidenced by community analysis and PHB yield. Using nitrogen gas as the nitrogen source also provides cost benefits for scale-up of bioplastic production. According to one aspect of the invention, the nitrogen source can include ammonium, hydroxylamine, nitrite, or elemental nitrogen.

Example carbon sources in various embodiments include methane, propane, acetate, etc. Example limiting nutrients during the unbalanced growth phase would include nitrogen, phosphorus, and metals, such as calcium, copper, potassium, iron, magnesium, and sulfur.

The invention has a wide range of useful applications. Polyhydroxyalkanoates (PHAs) are intracellular carbon and energy storage compounds synthesized by many bacteria and accumulated as granules. Over 100 PHAs have been identified. They are similar in their physicochemical properties to some synthetic plastics, e.g. polypropylene and polyethylene.

Because PHA molecules have a linear structure, and a monomer unit (repeated 100 to 30,000 times), they have thermoplastic properties, allowing them to be molded or extruded into valuable products without the need for stabilizers, fillers, or dyes.

This process, according to one embodiment of the invention, enables enrichment and maintenance of microbial communities capable of PHA production under non-sterile operational conditions over extended time periods. Conversely other processes that produce PHAs use pure cultures, require well-defined feedstocks and aseptic process conditions, have high substrate costs, expensive equipment, and high energy consumption, and are thus may be less attractive for scale-up and production.

In one example a high throughput technique to evaluate selection for PHB producing methanotrophs under a variety of nitrogen sources and concentrations was used. The example experiments were run at two gas levels, 5% oxygen/95% methane and 25% oxygen/75% methane. Nile red fluorescence is used as a proxy for PHB production per cell (see FIGS. 1a-1d and FIGS. 3a-3e), and is adjusted by the optical density of the culture to account for total biomass (see FIGS. 2a-2d and FIGS. 4a-4e).

FIGS. 1a-1d and FIGS. 2a-2d show competition among known mixed cultures, according to one embodiment of the invention. Two strains of PHB producing type II methanotrophs were combined with two strains of non-producing type I methanotrophs and allowed to compete under a variety of conditions. The results are compared to pure culture controls grown with 10 μM nitrate as the sole nitrogen source.

FIGS. 3a-3e and FIGS. 4a-4e show enrichments from activated sludge containing a diverse and unquantified consortium of methanotrophs and other organisms, according to one embodiment of the invention.

Enrichments labeled +nitrate contained 10 μM nitrate and were augmented with the specified concentration of either hydroxylamine or ammonium.

The results show that in known mixed cultures, growth on urea alone induced the highest PHB production. In enrichment cultures, growth on ammonium and ammonium+nitrate induced the highest PHB production. In enrichment cultures, growth on hydroxylamine+nitrate induced higher fluorescence than growth on nitrate alone.

In the description of the present invention, the term "biodegradation" is defined as a breaking down of organic substances by living organisms, e.g., bacteria. In the present context, biodegradation is intended to include anaerobic fermentation. Similarly, "biosynthesis" is defined as a production of chemical compounds from simpler reagents by living organisms, e.g., bacteria.

To understand the conditions required for PHA production, it is helpful to define the terms "growth", "balanced growth", and "unbalanced growth". "Growth" is defined as an increase in cell mass. This may occur through cell division (replication) and the formation of new cells during "balanced growth", or, during "unbalanced growth", when cellular mass increases due to the accumulation of a polymer, such as PHA. In the latter case, growth may be manifest as an increase in cell size due to the accumulation of biopolymer within the cell.

During balanced cell growth, all of the feedstocks (electron donors and electron acceptors) and all of the nutrients are present in the ratios required to make all of the macromolecular components of the cell. No feedstock or nutrient limits the synthesis of proteins, complex carbohydrate polymers, fats, or nucleic acids.

During unbalanced cell growth, a feedstock or nutrient needed to make one or more of the macromolecules is not present in the ratio required for balanced growth. This feedstock or nutrient therefore becomes limiting, and is termed the "limiting nutrient". Some cells may still achieve net growth under these conditions, but the growth is unbalanced, with accumulation of polymers that can be synthesized in the absence of the limiting feedstock or nutrient. These polymers include intracellular storage products, such as the polyhydroxyalkanoates (PHAs)—polyhydroxybutyrate (PHB), polyhdroxyvalerate (PHV), and polyhydroxyhexanoate (PHHx)—glycogen, or secreted materials, such as extracellular polysaccharide.

As an example of balanced and unbalanced growth conditions consider the nitrogen requirement for balanced cell growth. Nitrogen constitutes about 12% of dry cell weight. This means that in order to grow 100 mg/L cell dry weight, 12 mg/L of N must be supplied along with a feedstock and other nutrients in the required stoichiometric ratios. If other feedstock and nutrients are available in the quantities needed to produce 100 mg/L of cell dry weight, but less than 12 mg/L of N is provided, then unbalanced cell growth may occur, with accumulation of polymers that do not contain N. If N is subsequently provided, the stored polymer may serve as feedstock for the cell, allowing balanced growth, with replication and production of new cells.

In one aspect, the present invention provides a cost-effective method for the production of PHB using methane as a source of carbon. The methane is preferably derived from biodegradation of organic waste.

According to one aspect of the invention, the biotransformation process includes using waste materials, which may include both biocomposite waste materials as well as other organic solid waste materials are collected in a modern landfill or anaerobic digester where they undergo anaerobic microbial biodegradation.

According to one embodiment, landfill may be used to biodegrade the waste materials. The landfill is positioned in the ground just below the surface. A liner forms the walls of the landfill into which the organic waste such as biocomposite is placed. A methane gas collector is used to collect methane degradation product of the biodegradation. The methane is then fed from the landfill using a methane collection tube, for example. A tube or similar apparatus is used for leachate collection.

A conventional anaerobic digester may be used for the biodegradation of waste materials to produce methane gas and digested sludge as anaerobic degradation products.

In a further aspect, anaerobic degradation products of the biodegradation include methane and volatile fatty acids, e.g., acetic and propionic acids. The degradation products are collected and may be stored temporarily and/or transported. In some cases the degradation products may be combined with anaerobic fermentation products derived from other organic waste products, such as agricultural waste streams or treated wastewater, to form a feedstock for subsequent biosynthesis of. The feedstock may be used immediately, stored, or transported.

The use of methane and/or volatile fatty acids as a carbon source in the feedstock makes the biosynthesis process less expensive as compared with other microbial biosynthesis processes that use more expensive carbon sources. Methane also can be continuously generated and delivered to a batch culture as a uniform feedstock for growth of methanotrophs and PHA production. The feedstock is used in aerobic microbial biosynthesis of PHA polymers using a mixed bacterial community, preferably including methanotrophs. The PHA is grown under unbalanced growth conditions, i.e., when an essential nutrient is deficient or when toxic stressors are present. The biosynthesis may be performed using a small-scale fermentation facility.

PHA granules are extracted from the biosynthesized bacterial PHA, e.g., using surfactant treatment to remove much of the protein followed by sodium hypochlorite digestion to remove most of the remaining protein, which leaves PHA granules intact. The alkaline waste stream that results from this process would likely be amenable to anaerobic digestion to methane, which could be collected and recycled as part of feedstock. Alternatively, other PHA granule extraction methods based on acid-base extraction and sonication may be used. PHA may also be recovered from cell debris by supercritical $CO_2$ extraction.

Mechanical properties of a PHA resin matrix can be altered through copolymerization with other hydroxylalkanoate monomers or with reactive polymer blending. For example, when PHB is copolymerized with hydroxyvalerate (HV) or hydroxyhexanoate (HHx), the ductility, toughness, and ease of molding increase while the crystallinity and melting point decrease.

The bacterial storage polymer poly-b-hydroxybutyrate (PHB) can be extracted and used as a biodegradable plastic for applications ranging from disposable eating utensils to furniture. Commercially, PHB granules have value as plastics or resins, with properties similar to petrochemical plastics.

Turning now to a more detailed description of certain specific techniques related to the method for biosynthesis of PHA. Preferably, embodiments of the biosynthesis method use a bacterial community including a variety of methanotrophs that produce the highest levels of PHB (i.e., high ratios of grams PHB to grams biomass). This would specifically include the Type II methanotrophs, which use a carbon assimilation pathway that feeds into the biosynthetic pathway for PHB production. Other bacteria used in the biosynthesis of PHA are enriched by growth upon the specific biodegradation products of the biodegradation process. The use of mixed bacterial cultures makes the process less expensive as compared with processes that use pure cultures by eliminating the need for maintenance of special cultures. In the context of the present description, the term "mixed cultures" is defined to include bacterial communities containing a variety of distinct cultures or species, irrespective of whether or not the species are well-defined. The term "mixed cultures" also includes enrichment communities. These are communities of organisms subjected to selective pressures favorable for the growth of organisms that positively affect PHA production and unfavorable for the growth of organisms that negatively affect PHA production.

The bacterial cultures may be derived from biomass from various sources. Methanotrophs are found in environments where both oxygen and methane are present, often at the interface between aerobic and anaerobic zones. They are common in rice paddies, swamps and marshes, surface sediments in ponds and lakes, activated sludge, and meadow and deciduous forest soils, including freshwater, brackish, and saline environments, deserts, landfills, coal mine surfaces, and oceans. The invention uses sources that include those environments subject to periodic stress, such as carbon, nutrient, or oxygen limitation. The invention further uses environments with periodic stresses, such as intermittent availability of methane or water, to select for methanotrophs that can store carbon for use during such times of stress. The methanotrophs isolated from environments with these different selection pressures have different rates and yields of PHB production.

According to one aspect of the invention, samples of methanotrophs from diverse environments can be screened for their capacity to produce PHBs and to identify cultures capable of producing commercially significant levels of PHB.

Cultures may be grown to high density, subjected to nutrient limitation (e.g., nitrogen and phosphorus), and screened for PHA production in aerobic shake flask cultures.

Methanotrophs are classified into three groups based on their carbon assimilation pathways and internal membrane structure: Type I (gamma proteobacteria), Type II (alpha proteobacteria), and a subset of type I known as Type X (gamma proteobacteria). Type I methanotrophs use the RuMP pathway for carbon assimilation whereas Type II methanotrophs use the serine pathway. Type X methanotrophs use the RuMP pathway but also express low levels of enzymes found in the serine pathway. Type II methanotrophs accumulate PHB.

In one embodiment, methanotroph enrichments from different environments are introduced into a sequencing bioreactor with minimal media and are forced to cycle between two phases: a first phase in which methane is supplied in excess while nitrogen is absent (or significantly reduced) and a second phase in which the flow of methane is stopped (or significantly reduced) and a pulse of nitrogen is added. This cycling is used to select for bacteria that store PHB when nitrogen is absent and subsequently use the PHB to produce new biomass when nitrogen is introduced to the system, thus conferring a competitive advantage on those organisms that produce higher quantities of PHB during the period of methane addition. In one embodiment, nitrogen is preferably selected as the limiting nutrient because its absence is known to induce PHB production and it can be easily monitored. Because the reactor is intrinsically designed to select for PHB-producing methanotrophs, it can be maintained as an open, non-sterile system, thus avoiding the costs and difficulties associated with maintaining a sterile culture during industrial production of PHB. Shifts in community composition may be monitored using a wide range of methods including terminal restriction fragment length polymorphism (T-RFLP) analysis of pmoA, clone libraries, and microarrays. System performance may be monitored by measuring the PHB content of the cells.

Preferably, a methane-fed culture grown to high cell density is used to produce high percentages of PHA when supplemented with acetate and/or propionate, and limited for nitrogen or phosphorus. The most effective culture is one with high PHA yield, high rate of PHA production, high growth rate, and high fitness, allowing robust non-sterile operation.

This may be achieved by allowing communities to adapt to an environment that provides a selective advantage for PHA production. The biosynthesis may be performed in a bioreactor with conditions maintained to favor high levels of PHA production under non-sterile growth conditions in rapid, high cell density fermentations.

A range of bioreactor configurations may be used, including sequencing membrane bioreactors and a continuous multistage dispersed growth configuration. In one embodiment, the bioreactor is operated to select for bacteria that efficiently produce PHB from methane, i.e., the bioreactor conditions select against bacteria that either do not produce PHBs from methane or produce them inefficiently. In a further aspect of the invention, the bioreactor is operated as a sequencing batch bioreactor. For example, sequencing batch reactors can be operated by repeatedly cycling through two periods. In the first period of cycle n, methane is provided in excess, but no nutrients. Methanotrophs are able to accumulate PHB under these conditions enlarge. At the end of the first period a portion of the bacteria are harvested as waste cells and PHB is extracted. In the second period nutrients are provided but no methane. The bacteria are able to use their stored PHB to replicate during this phase and to maintain cell function, while other bacteria with smaller amounts of stored PHB will replicate less and are subject to cell decay as they cannot meet the energy demands for cell maintenance. The two periods are then repeated in cycle n+1, and so on. Repeated cycling through these periods will select for bacteria that produce enough PHB in the first period to replicate during the second period of carbon starvation. Additional species may be periodically introduced, e.g. at the beginning of the first period of a cycle. Organisms able to produce more PHBs more quickly should become dominant. Operating the system in a non-sterile manner ensures that the dominant species has a high relative fitness. Different methanotrophs will likely produce PHB with differing molecular weight distributions or potentially other PHA polymers. Consequently, the suitability of the PHA polymers for particular target applications serves as an additional criterion for subsequent selection of cultures.

Because the rate of cellular PHB utilization for growth is directly proportional to the PHB content of a cell, cells with a higher percent of dry weight of PHB will reproduce more quickly and species that accumulate a higher percentage of PHBs will have a selective advantage over other species. This advantage can be accentuated by gradually lengthening the time period without methane, creating a penalty for rapid PHB degradation and an incentive for PHB accumulation. In activated sludge systems, bacteria respond to periods of substrate excess ("feast") and deficiency ("famine") by storing PHBs during the substrate excess period and using them to make new cells during the substrate deficient period. The term "excess" in this context means that the feedstock and all other nutrients (except a limiting nutrient) are present at a level sufficient for balanced growth. The term "limited" or "deficiency" in this context means that a nutrient is present at a level that is less than needed for balanced growth. During a feedstock limitation, sufficient nutrients are present when there is enough to deplete the polymer previously stored under unbalanced growth conditions. The exact amount will depend on the amount of polymer storage that has occurred.

In addition to creating an environment that selects for methanotrophic species that produce PHB, evolution of dominant species may occur as mutations confer selective advantages on daughter strains that outcompete the parent strains. Operation is expected to evolve a robust, PHB-producing methanotroph or a mixed culture that is better able to produce PHBs than the parent culture. Species compete against one another in an environment designed to select for the desired characteristics.

In one embodiment, a set of sequencing batch reactors may be operated to select for organisms that accumulate PHBs rapidly and at high yield and to enable competition of different species of PHB-producing methanotrophic bacteria. Operation may be managed so that PHB-producing bacteria have a selective advantage over those that do not. This may be accomplished by sequencing through two periods; a first period in which methane is present in excess but nutrients are absent and a second period in which nutrients are present but methane is absent. During the first period, PHB-producing bacteria accumulate PHBs; during the second period, the organisms that accumulated PHBs are able to produce protein and replicate while cells that did not store PHB are unable to replicate because they lack carbon. Repeated cycling between these phases with periodic biomass-wasting at the end of the methane feed period select for bacteria that produce enough PHBs to replicate during the period of carbon starvation.

The reactor sequences between periods of carbon excess with methane provided, and periods of carbon starvation with nutrients provided. The effect of competition in successive cycles results in cells that are unable to accumulate significant quantities of PHB and thus are not able to replicate in the nutrient-sufficient phase.

In some embodiments, the system is inoculated with an enrichment, where additional species and mixed cultures are periodically introduced, at concentrations comparable to the concentration of the cells in the reactor. Prior to the addition of new cultures, an additional fraction of the existing cells are wasted. The PHB content of the wasted cells can then be measured using a spectrofluorometric assay and the relative abundance of species is monitored by T-RFLP analysis. Organisms that are able to produce more PHB more quickly and to a higher level become dominant. By operating the system in a non-sterile manner, the dominant species has a high relative fitness and has characteristics that would be desirable in an industrial system. Regularly obtained samples may be archived to permit detailed analyses of shifts in community structure that may correspond to enhancements or changes in PHB production.

PHAs from the most promising cultures may be characterized for monomer composition, molecular weight distribution, and other parameters important to bioplastic applications. The results of these examples assist in the identification of cultures and strains for optimization of bioreactor operation and scale-up.

Information on phylogeny can be used to identify organisms, determine ecological relationship, and optimize PHB production.

Desired reactor configurations and operation select for the most promising culture that enable high levels of PHA production with minimal energy inputs. Also of interest are cultures that produce PHA polymer blends or copolymers that are particularly well suited for specific applications.

In another embodiment of a sequencing batch reactor for PHB production from methane, pH, DO (mixing), and temperature control are provided. The reactor includes a vessel, a mixer, a valved nutrient inlet, a valved PHB and waste outlet, an oxygen inlet, and a valved methane inlet.

According to one method of PHB production, during a first period, nutrients (e.g., N and P) are added through opened inlet 404 while methane inlet 410 and harvesting outlet are closed. The mixture volume increases during this period, causing the mixture level in the reactor to rise from the base level $V_0$. In a second period, methane is added through open inlet and PHB accumulates while nutrient inlet are harvesting outlet are closed. The mixture volume increases further during this period, causing the mixture level in the reactor to rise to the full level $V_f$. Although no nutrients are added in the second period, some residual nutrients may still be present in the reactor. In a third period, the cultures are harvested by extracting PHB and waste cells from open harvesting outlet while the nutrient inlet and methane inlet are closed. The volume decreases during this final period, dropping down from level $V_f$ to the base level $V_0$. The cycle then repeats.

According to another method of PHB production, during a first period, nutrients (e.g., N and P) are added through opened inlet while methane inlet and harvesting outlet are closed. The mixture volume increases during this period, causing the mixture level in the reactor to rise from the base level $V_0$ to level $V_c$. In a second period, nutrients are added through opened inlet and methane is added through open inlet while harvesting is closed. The mixture volume increases further during this period, causing the mixture level in the reactor to rise from level $V_c$ to the full level $V_f$. In a third period, methane is added through open inlet while PHB accumulates in the cells. In a fourth period, the cultures are harvested by extracting PHB and waste cells from open harvesting outlet while the nutrient inlet and methane 410 are closed. The volume decreases during this final period, dropping down from level $V_f$ to the base level $V_0$. The cycle then repeats.

According to another technique of the invention, cell mass may be extracted from the sequencing reactor, then the extracted portion grown with complete nutrients to increase cell density, and then subjected nutrient limitation. This procedure involves taking samples from the reactor and using the samples for batch incubations to produce PHB.

Bioreactors may range from small bench-scale bioreactors to large-scale commercial production bioreactors, and also be of various types, including sequencing membrane bioreactors and a continuous multistage dispersed growth configuration. In larger scale bioreactors (i.e., fermentation volumes of tens of liters or more) mass transfer of poorly soluble gases (methane and oxygen) may be improved by delivery under pressure or via "dry" fermentations using gas phase delivery of methane and oxygen, and cell densities may be increased using ultrafiltration membrane modules (hollow fiber or flat sheet) for cell separation and concentration.

By way of illustration of the principles of the present invention, a specific example of PHB production using a bench-scale bioreactor will be described. A bench-scale bioreactor (1 L working volume) was cycled daily between periods of 1) methane addition and nitrogen starvation (~16 hours) and 2) methane starvation with nitrate addition (~8 hours). A small fraction of the volume (~50 mL) was sampled twice daily, at the beginning of each period, and was replaced with equivalent media daily. The wasted cells were frozen for analysis of biomass and PHB concentration. The concentration of nitrate in the reactor was monitored daily. Biomass pellets were archived throughout the experiment. DNA was later extracted from these pellets and Terminal Restriction Fragment Length Polymorphism (T-RFLP) with the restriction enzyme Alu I was used to characterize the community within the reactor.

The bioreactor was inoculated with a methanotroph enrichment culture that had previously been shown to produce ~30% PHB under nutrient limitation. After inoculation, the reactor was maintained under non-sterile conditions. No additional cultures were intentionally introduced into the system.

This experiment demonstrated that a PHB-producing methanotrophic culture can be maintained under the previously described cycling conditions for a period of 59 days. The levels of biomass within the system were controlled by the nitrate addition and additional wasting events. The PHB content of the cells (g PHB/g total biomass) fluctuated throughout the experiment but typically remained above 20%.

T-RFLP analysis showed that the community within the reactor was relatively stable. A detailed analysis of individual cycles shows that the PHB content of the system fluctuated daily as expected: PHB content increased during the period of methane addition/nitrogen starvation and decreased during the period of methane starvation/nitrogen addition.

This embodiment of the invention selects for PHA-accumulating bacteria grown on common anaerobic degradation products, specifically volatile fatty acids, such as acetate and propionate, and methane gas. Continuous or sequencing batch reactors are operated under non-sterile conditions so as to create selection conditions favorable for organisms that accumulate PHA.

A selective advantage is conferred upon PHA-accumulating microorganism by sequencing through two stages a first stage in which the carbon source (i.e. volatile fatty acids and/or methane) is present in excess but nutrients are absent and a second stage in which nutrients are present but the carbon source is absent. During the first stage, PHA-producing bacteria accumulate PHAs during the second stage, the organisms that accumulated PHAs are able to produce protein and replicate while cells that did not store PHA are unable to produce protein and replicate because they lack carbon. Repeated cycling between these phases selects for microorganisms that produce PHA in order to replicate during the period of carbon starvation. PHA is harvested from the biomass at the end of the carbon feed period or stage.

Using the present embodiment, bioreactors can operate under conditions that select against microorganisms that do not produce PHA, enabling non-sterile production of PHAs and, over the long term, tend to select for organisms that can store PHAs at high levels. The cost of producing PHA using low-cost carbon sources (e.g., products of anaerobic degradation, particularly, methane) and a nonsterile process is expected to be lower than previous production methods. Methane is widely available at low cost, and it is the major product of anaerobic degradation of organic wastes. Moreover, under anaerobic conditions such as those inside a wet landfill or an anaerobic digester, organic wastes including PHB-containing products degrade to methane. Aerobic methane-consuming bacteria can convert methane into PHB, completing a "cradle-to-cradle" carbon cycle.

Projected benefits of this cycle include decreased pollution and aesthetic nuisance caused by petrochemical plastics, additional incentives for capture of methane (a major greenhouse gas), decreased $CO_2$ emissions, decreased energy usage, decreased dependence on petrochemicals, decreased demand for wood, and extended landfill life.

According to another embodiment, the selection strategy for PHA-producing bacteria includes a pulsed carbon source. Here, a strategy is provided where the carbon source is supplied continuously and a key nutrient, such as nitrogen, is pulsed. This embodiment presents a new strategy for PHA accumulation in a continuous reactor where the carbon source is supplied continuously and a key nutrient is pulsed.

In the past, microbial production of polyester bioplastics have used a 2-step fermentation: (1) a balanced growth step in which all nutrients and feedstock required for balanced cell replication are supplied, and the bacteria are thus able to replicate and divide, and (2) an unbalanced growth step in which a carbon feedstock is provided, but one or more essential nutrients required for cell replication is not supplied, thus preventing cell replication. Examples of limiting nutrients include nitrogen, phosphorus, sulfur, iron, sodium, potassium, calcium, magnesium, copper and manganese.

During unbalanced growth, many bacteria can produce storage granules made of one or more PHA polymers that include PHB, PHV (polyhydroxyvalerate), or PHHx (polyhydroxyhexanoate). These granules can be harvested, and the resulting material used as a biodegradable substitute for non-biodegradable plastics derived from petrochemical feedstocks, such as polypropylene and polyethylene.

It is theorized that PHA granules confer a competitive advantage for cells possessing them when these cells are subject to periodic carbon starvation. Strategies for selection of PHA accumulators based on this theory involve subjecting the cells to intermittent periods of carbon starvation.

It is observed by the inventors that, with cultures of Type II methanotrophs, accumulation of PHB under conditions of continuous carbon surplus occurs. PHB was found to accumulate under conditions of nutrient deprivation but it degraded slowly when nutrients were present and methane was absent. When methane was also present, the PHB was used rapidly. The results suggest a distinctive role for PHB in Type II methanotrophs. Since these organisms require reducing power for the oxidation of methane by the enzyme methane monooxygenase, it is likely that the PHB serves as a source of reducing power facilitating more rapid utilization of methane.

The present embodiment of the invention provides a new strategy for PHB accumulation in which methane or biogas is provided continuously to Type II methanotrophs, while a limiting nutrient, such as nitrogen, is provided intermittently. This process can be applied to the continuous production of the bioplastic PHB.

The configuration of the current embodiment enables an operational strategy in which methane/biogas is provided continuously, and nitrate or another limiting nutrient is supplied through intermittent pulses. The proposed operational modes impose a strong selection pressure against methanotrophs that do not produce PHB.

A second mode of operation, according to another embodiment, is based on the observation that PHB accumulating Type II methanotrophs can be selectively grown with $N_2$ as the source of nitrogen. When grown in this manner, these organisms continuously produce low-levels of PHB and growth rate is slow. The slow growth rate can be attributed to the energy costs associated with $N_2$ fixation. Faster growth is possible through continuous addition of methane/biogas and oxygen, together with alternating additions of nitrogen as $N_2$ (in air) and as nitrate.

According to another embodiment, a reactor is continuously supplied with methane and another nutrient, such as nitrogen, is supplied in pulses. In this variation, cells are not harvested for polymer extraction, but rather, the reactor serves as a seed reactor for cells that can be inoculated into a separate reactor and used for production of PHB. In some embodiments, the following process configurations may be desirable: 1) Continuous supply of methane (or biogas) and oxygen accompanied by intermittent pulsing of nitrogen supplied as nitrate. 2) Continuous supply of methane (or biogas) and air accompanied by intermittent pulsing of nitrogen supplied as nitrate.

In an example experiment, cells containing PHB were incubated with and without methane and with and without nitrate. In the absence of methane, it was expected that cells containing PHB would grow rapidly when they were fed nitrogen, but it was discovered that they grew slowly. It was also expected that these cells would not metabolize methane if they contained PHB, but they did so rapidly. In fact, the cells used the methane and the PHB simultaneously and at high rates.

These surprising new results demonstrate the innovative nature of the present invention. It is possible that different cultures will behave differently.

It had previously been assumed, based on other data, that the primary function of the PHA polymer was to provide carbon during periods of nutrient deficiency (unbalanced growth). It now appears that the polymer has a second function: it can be a source of electrons when there is a shortage of electrons.

The first step in the consumption of methane is its oxidation to methanol. This step is mediated by an enzyme called methane monooxygenase. This enzyme requires methane, oxygen, and electrons. So the rate of methane oxidation can be limited by the availability of methane, oxygen or electrons. These electrons are supplied inside the cell as NADH.

Recent data suggest that oxidation of PHB can provide the electrons needed for rapid reduction of NAD into NADH. This implies that PHB stored during a period of nitrogen deficiency may be used to accelerate methane oxidation when nitrogen becomes available. In mixed cultures, the competition for methane is fierce. The winner is the organism that can use methane fastest. If the availability of electrons is limiting the rate of methane oxidation then storage of electrons as PHB during nitrogen deficient periods makes sense because its oxidation can be used to reduce NAD to NADH, allowing more rapid formation of a key reactant needed for methane oxidation.

It's also possible that simultaneous metabolism of PHA granules and methane allows cells to "optimize" their biochemical pathways for both the production and use of ATP.

Poly(3-hydroxy)butyrate is a high molecular weight carbon storage polymer produced by a wide variety of microorganisms and useful as a commercial thermoplastic. PHB production by methanotrophic organisms allows for production of high value polymer from a low cost feedstock of methane gas. Production of PHB by methanotrophs grown in open, mixed culture systems is contingent upon initial selection of PHB producing organisms from a diverse inoculum and subsequent resistance to invasion by non-PHB producing organisms. This robustly selects and maintains communities of PHB producing methanotrophs while allowing growth at high rates and densities.

Methanotrophic bacteria naturally produce PHB as a carbon and energy storage polymer under conditions of unbalanced growth. Production of PHB is contingent upon selection of PHB producing Type II methanotrophs, as opposed to type I methanotrophs, which are not known to produce PHB. In a further embodiment of the invention, cells are originally enriched with ammonium as the sole nitrogen source. Growth on ammonium or growth in the presence of hydroxylamine selects for PHB producing methanotrophs by dramatically inhibiting the growth and survival of type I organisms. Because growth of type II methanotrophs is also slow on ammonium or in the presence of hydroxylamine, the cells are then transferred to growth on nitrate or urea, both of which allow for rapid growth of dense cultures followed by PHB production when all nitrogen is exhausted. By cycling between multiple nitrogen sources it is possible to maintain a mixed culture of PHB producing methanotrophs without sacrificing density, growth rates, or total PHB production.

PHB production in methanotrophs is limited exclusively to strains in the Type II group that include the genera *methylocystis, mythylosinus*, and *methylocapsa*. Under the mesophilic conditions most favorable for rapid growth of dense methanotrophic cultures, Type I organisms tend to dominate, hindering long term study of mixed cultures. In the past, experiments have been conducted using pure cultures or known enrichment cultures in which Type I organisms are deliberately excluded. While this strategy allows for short term study, despite best efforts such cultures inevitably become contaminated in the longer term, usually within 2-4 weeks. In addition, use of pure and known mixed cultures limits biodiversity as compared to the use of highly diverse unknown mixed culture. This lack of genetic diversity adversely affects our ability to select for fast-growing strains capable of high PHB production. Establishment of a selective regime that effectively suppresses growth of Type I organisms is also a critical to minimizing the cost of industrial scale production, due to the high costs associated with maintaining sterile reactor conditions.

Established selection techniques are currently incompatible with the goals of high growth and high PHB production.

Selection techniques showing some degree of effectiveness include growth with no copper, growth in dilute medium, growth using gaseous nitrogen as the sole nitrogen source, and growth at low pH. All of these selection techniques suppress the growth of Type I organisms at the expense of reduced growth in Type II organisms. In addition, methods based on dilute media, low pH, or limitation of copper are difficult to implement even at bench scale, while nitrogen fixation is unreliable as a selector.

Selection based on nitrogen sources represents one alternative to these methods. Recent research on the genome for the type II organism *Methylosinus trichosporium* OB3b contains the pathway for hydroxylamine reduction to ammonium, while type I organisms appear incapable of reducing hydroxylamine and instead oxidize it to form nitrite, another toxic intermediate. Toxic hydroxylamine is produced as a byproduct of methane oxidation when ammonium is oxidized by the non-specific methane monooxygenase. The ability to detoxify hydroxylamine by reduction to ammonium is a potential competitive advantage for type II organisms in ammonium rich environments. Both ammonium and urea are inexpensive nitrogen sources that should produce higher yields than nitrate due to their reduced state. These nitrogen sources were implemented for their ability to select for high densities of PHB producing Type II organisms.

In one example to determine the effectiveness of varying nitrogen sources as a selection mechanism, competition experiments were conducted using a known mixed culture of two Type I and two Type II strains (see FIGS. 1b-1d) and an unknown enrichment from activated sludge (see FIGS. 3a-3d). A high throughput growth and analysis system was employed to determine PHB production, with 8 nitrogen concentrations tested at two oxygen levels and 4 replicates per condition. In known mixed culture, growth on 5 mM urea and 25% oxygen was the most effective selector for PHB production, with mixed results for nitrate and little growth observed in cultures grown on ammonium. Metabolism of urea requires cleavage into two molecules of ammonium and one molecule of carbon dioxide, and it is therefore possible that growth on urea creates a slow supply of ammonium suitable for growth of Type II methanotrophs while still inhibitory towards the Type I cultures. Alternatively, it is possible that the Type I cultures in this experiment lacked the pathways necessary to process either urea or ammonium.

Results differed substantially in cultures enriched from activated sludge, with the highest fluorescence observed in cultures grown with 5 mM ammonium. No elevated fluorescence was observed in cultures grown on urea as compared to nitrate. In cultures grown with varying levels of ammonium in addition to 10 mM nitrate, fluorescence was substantially elevated as compared to cultures grown on 10 mM nitrate alone, particularly at 2 mM ammonium and above.

Due to the promising results small volumes of the microplate enrichments, further enrichments were conducted in 4 L fermenters to allow for more diversity in the inoculum and to more effectively quantify the resulting communities. Fermenters containing 10 mM of ammonium, urea, and nitrate were inoculated with activated sludge and allowed to reach plateau phase. The resulting cultures were analyzed for PHB content, biomass, and community composition. Cultures enriched with nitrate showed dense growth of up to ~4 g/L but failed to produce measurable PHB (see Table 1). Cultures grown on ammonium grew only to low densities up to ~0.4 g/L, but did produce PHB in one replicate. Cultures enriched on urea showed both results, with one enrichment growing to high density while the remaining two struggled. While molecular analysis is in progress, a cursory visual analysis indicates that low density cultures were cloudy white, while high density cultures were a pink or orange color characteristic of Type I methanotrophs. This analysis is consistent with the hypothesis of Type II organisms in the low density ammonium and urea cultures and Type I organisms in the high density urea and nitrate cultures.

Based on these results, it is apparent that growth on ammonium selects for Type II methanotrophs but inhibits their growth and PHB production. Nitrate enrichments grew much more rapidly but failed to produce PHB. It is therefore beneficial to combine growth on ammonium with growth on nitrate, to both inhibit Type II organisms and encourage rapid growth. Two regimes were tested based on this hypothesis, one in which ammonium and nitrate were applied simultaneously and one in which cells were enriched on ammonium and then amended with nitrate. Two of the three enrichments grown with both nitrogen sources at once demonstrated PHB production, but at very low levels. When the two nitrogen sources were applied in sequence, significantly higher PHB production was observed, particularly in the enrichment containing the highest level of ammonium. In this enrichment PHB production was measured at 10% in a dense culture of 2.85 g/L TSS.

TABLE I

| Sample | Enrichment number | Biomass (g/L) | Percent PHB | Total PHB (g/L) |
|---|---|---|---|---|
| 10 mM Ammonium | 1 | 0.36 | 3.1% | 0.01 |
| 10 mM Ammonium | 2 | 0.37 | 0.0% | 0.00 |
| 10 mM Ammonium | 3 | 0.27 | 0.0% | 0.00 |
| 10 mM Urea | 1 | 0.35 | 0.0% | 0.00 |
| 10 mM Urea | 2 | 0.11 | 0.0% | 0.00 |
| 10 mM Urea | 3 | 3.65 | 0.0% | 0.00 |
| 10 mM Nitrate | 1 | 1.51 | 0.0% | 0.00 |
| 10 mM Nitrate | 2 | 3.94 | 0.0% | 0.00 |
| 10 mM Nitrate | 3 | 3.30 | 0.0% | 0.00 |
| 1 mM ammonium + 10 mM nitrate | 4 | 1.87 | 1.8% | 0.03 |
| 4 mM ammonium + 10 mM nitrate | 4 | 1.43 | 1.5% | 0.02 |
| 10 mM ammonium + 10 mM nitrate | 4 | 0.39 | 0.0% | 0.00 |
| 2 mM ammonium | 5 | 0.32 | 3.2% | 0.01 |
| 5 mM ammonium | 5 | 0.21 | 0.0% | 0.00 |
| 10 mM ammonium | 5 | 0.35 | 0.0% | 0.00 |
| 2 mM ammonium -> 10 mM nitrate | 5 | 2.55 | 3.1% | 0.08 |
| 5 mM ammonium -> 10 mM nitrate | 5 | 3.77 | 3.0% | 0.11 |
| 10 mM ammonium -> 10 mM nitrate | 5 | 2.85 | 10.0% | 0.28 |

Based on the success of sequential growth on ammonium and nitrate, the 10 mM ammonium→10 mM nitrate reactor was left in operation, cycling between one day of growth on ammonium and two days of growth on nitrate. After four cycles, a new reactor was inoculated from the original, this one cycling between ammonium and urea.

Figure 5:
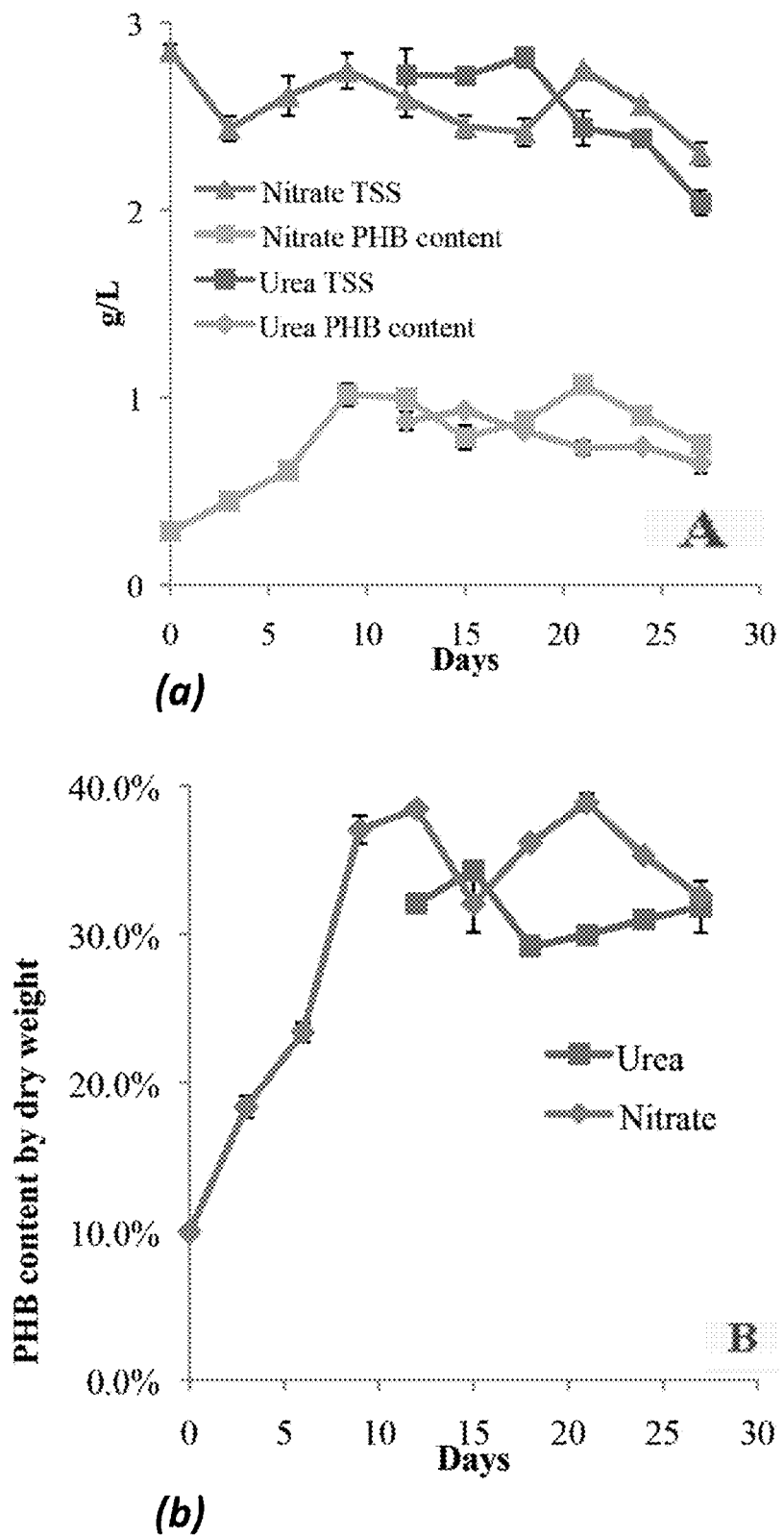
FIGS. 5a-5b show total suspended solids (FIG. 5a) and PHB production (FIG. 5b) in cycling reactors over time operated on a 3-day cycle in which cells were diluted 3:1 and grown on 10 mM ammonium for 24 hours, then diluted 3:1 again and grown on 8 mM nitrate or 4 mM urea for 48 hours and urea cycling reactor was inoculated from the nitrate reactor after 4 cycles, according to one embodiment of the invention.

Both reactors were successful at selecting and maintaining a dense, PHB producing culture (see FIGS. 5a-5b). In the nitrate cycling reactor, PHB production rose from 10% initially to a high of 39%, with a maximum of 1.07 g/L PHB produced at the end of cycle. The urea reactor was similarly productive, producing up to 34% PHB and 0.93 g/L PHB. The nitrate cycling reactor has run for a full month with no indication of contamination.

Figure 6:
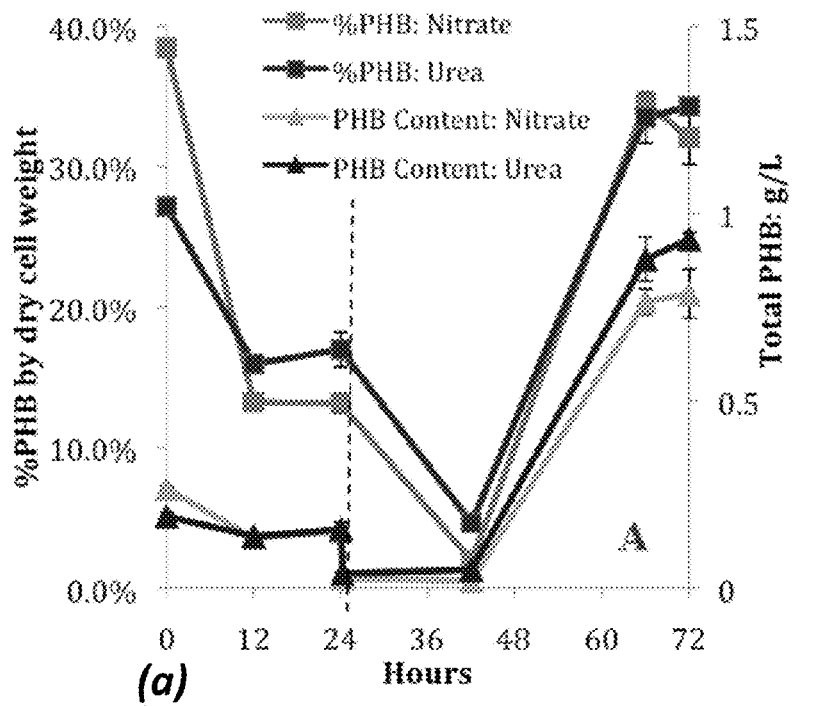
FIGS. 6a-6b show cell concentrations and percent PHB by dry cell weight in two cycling bioreactors over the course of a single cycle with the PHB content measured by flow cytometry and calibrated using gas chromatography and the ammonium phase for both reactors is shown left of the dashed line, while the nitrate/urea phase is to the right, according to one embodiment of the invention.
Figure 6:
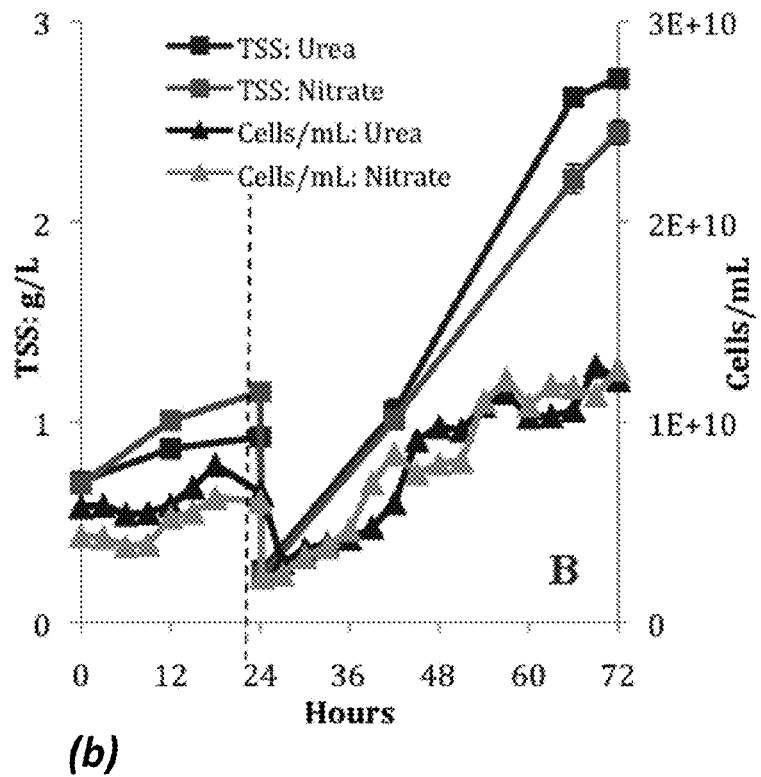

Looking more closely within each cycle, growth is slow during the ammonium phase, with only a slight increase in cell concentration and total suspended solids. Simultaneously, within the first 12 hours of ammonium exposure both PHB percentage by dry weight and total PHB levels declined significantly in both the urea and nitrate reactors. After the addition of nitrate, replication begins almost immediately in both reactors and continues at an exponential pace for 18 hours, after which cell growth tapers and PHB production begins due to exhaustion of available nitrogen sources. Growth on nitrate does not display the lag phase present in previous experiments, indicating that growth on ammonium was sufficient to replenish nitrogen levels and begin replication. It is likely that during growth on ammonium the PHB consumed was used as a source of reducing power for the reduction of hydroxylamine to ammonium, indicating a potentially unobserved use for stored PHB in methanotrophic organisms. Overall behavior in both reactors was remarkably similar, and urea offers a preferable nitrogen source do to its mild selective properties, low cost, and potential for higher yields through use of a reduced nitrogen source (see also FIGS. 6a-6b).

Establishment of an effective selective regime is a critical breakthrough with regard to the economical production of PHB by methanotrophs. These reactors require no precautions to prevent contamination, and should instead incorporate outside species into a more efficient community. Such a system has the potential to vastly reduce capital costs by eliminating the need for sterilization, and could be operated at small scale by an inexperience operator. The example nitrate/ammonium cycling bioreactor continued stable operation for more than 30 days of operation. With PHB content stabilizing at 0.8-1.1 g/L and 3 L of culture produced every 3 days per bioreactor, production in this example is 1.6-2.2 grams per day of PHB in the two reactors.

Figure 7:
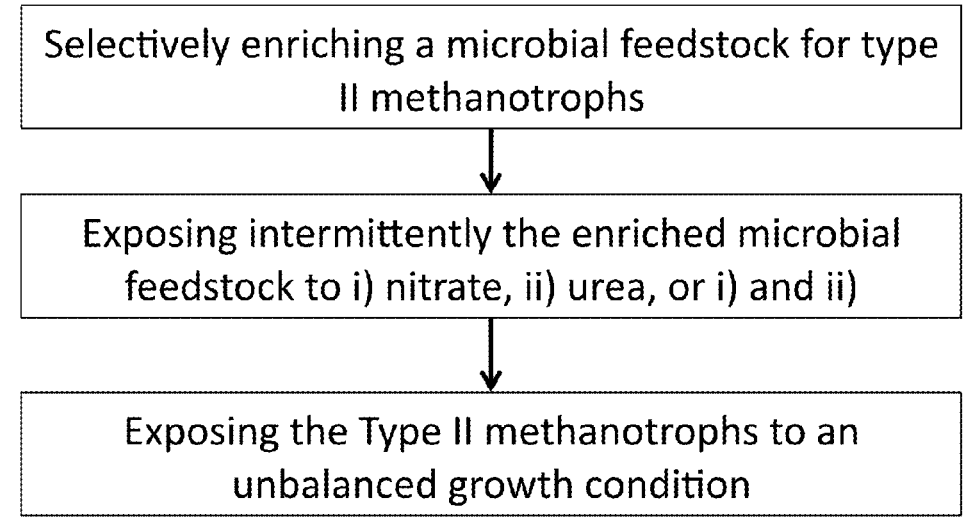
FIG. 7 shows a flow diagram of the method of selection for type II methanotrophs, according to one embodiment of the invention.

FIG. 7 shows a flow diagram of the method of selection for type II methanotrophs, according to one embodiment of the invention.

According to another embodiment of the invention, a method of selection for type II methanotrophs is provided that includes enriching a microbial feedstock, using a non-sterile bioreactor, with methane and a nitrogen source, where the microbial feedstock includes a mixture of Type I and Type II methanotrophic cells, where an inhibited growth of the Type I methanotrophic cells and an enhanced growth of the Type II methanotrophic cells forms, where the nitrogen source is varied periodically and/or the methane source is varied periodically. Regarding the periodic nitrogen variation, periodic nitrogen concentration reductions and concentration returns causes a partial pressure of the methane concentration to increase according to the reduction, where the methane partial pressure increase results in a decrease of the ammonium inhibition of the enhanced growth of said Type II methanotrophic cells. Alternatively, the periodic methane variation includes a methane concentration increase such that there is a reduction of the ammonium inhibition of the enhanced growth of the Type II methanotrophic cells.

Figure 8:
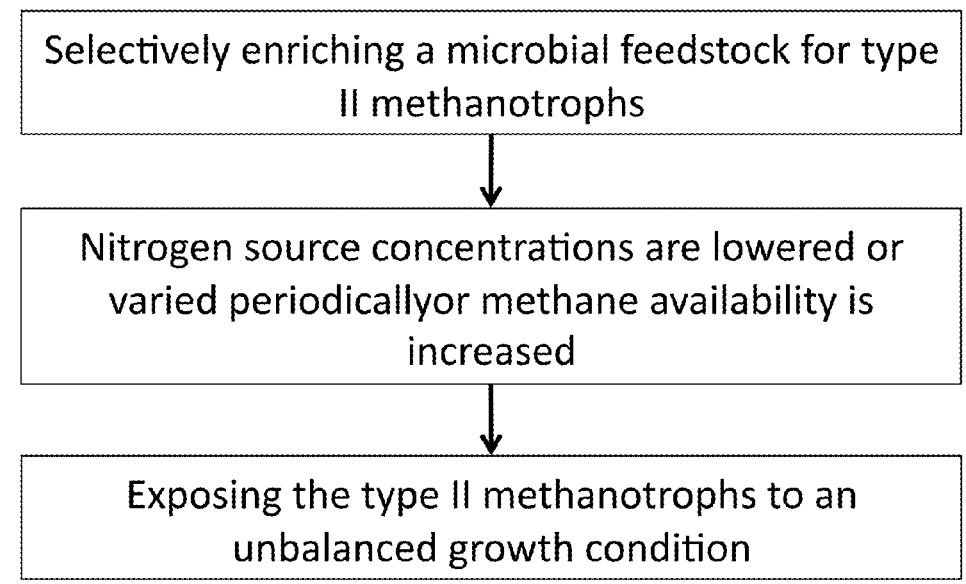
FIG. 8 shows a flow diagram of the method of selection for type II methanotrophs, according to another embodiment of the invention.

FIG. 8 shows a flow diagram of the method of selection for type II methanotrophs, according to another embodiment of the invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. All such variations are considered to be within the scope and spirit of the present invention as defined by the following claims and their legal equivalents.

What is claimed:

1. A method of selecting for type II methanotrophs and producing polyhydroxybutyrate, comprising:
    a. adding an effective amount of an ammonium source to a microbial feedstock within a bioreactor, wherein said microbial feedstock comprises a mixture of Type I and Type II methanotrophic cells, under conditions to enhance the growth of said Type II methanotrophic cells and inhibit the growth of said Type I methanotrophic cells;
    b. adding an effective amount of a nitrogen growth source selected from the group consisting of nitrate, urea, and a mixture thereof to the microbial feedstock, under conditions to allow uninhibited replication of said Type II methanotrophic cell to occur: and
    c. growing the replicated Type II methanotrophic cells in a cultural environment that is absent of nitrogen for a suitable period of time to produce the polyhydroxybutyrate.

2. The method according to claim 1, further comprising providing limited nutrients to the microbial feedstock during the uninhibited replication of said Type II methanotrophic cells.

3. The method according to claim 2, wherein said limited nutrients are selected from the group consisting of nitrogen, phosphorus, calcium, copper, potassium, iron, magnesium, and sulfur.

4. The method according to claim 1, wherein i) methane, ii) biogas, iii) methane and oxygen, or iv) biogas and oxygen is provided continuously during steps a through c.

5. The method according to claim 1, wherein methane or oxygen is reduced or eliminated in said bioreactor during step b.

6. The method according to claim 1, comprising varying concentrations of said nitrogen growth source are varied to promote growth of said Type II methanotrophic cells and inhibit growth of said type I methanotrophic cells.

7. The method of claim 1, wherein in step b, said adding comprises intermittently adding an effective amount of said nitrogen growth source.

* * * * *